United States Patent
Tun

(10) Patent No.: US 9,839,632 B2
(45) Date of Patent: Dec. 12, 2017

(54) METHODS AND COMPOSITIONS USING 4-AMINO-2-(2,6-DIOXO-PIPERIDINE-3-YL)-ISOINDOLINE-1,3-DIONE FOR TREATMENT AND MANAGEMENT OF CENTRAL NERVOUS SYSTEM CANCERS

(71) Applicant: CELGENE CORPORATION, Summit, NJ (US)

(72) Inventor: Han W. Tun, Jacksonville, FL (US)

(73) Assignee: Celgene Corporation, Summit, NJ (US)

( * ) Notice: Subject to any disclaimer, the term of this patent is extended or adjusted under 35 U.S.C. 154(b) by 0 days.

(21) Appl. No.: 14/781,898

(22) PCT Filed: Apr. 1, 2014

(86) PCT No.: PCT/US2014/032483
§ 371 (c)(1),
(2) Date: Oct. 1, 2015

(87) PCT Pub. No.: WO2014/165482
PCT Pub. Date: Oct. 9, 2014

(65) Prior Publication Data
US 2016/0045484 A1 Feb. 18, 2016

Related U.S. Application Data

(60) Provisional application No. 61/807,605, filed on Apr. 2, 2013.

(51) Int. Cl.
*A61K 31/545* (2006.01)
*A61K 39/395* (2006.01)
*A61K 31/454* (2006.01)
*A61K 45/06* (2006.01)
*A61K 31/573* (2006.01)

(52) U.S. Cl.
CPC .......... *A61K 31/454* (2013.01); *A61K 31/573* (2013.01); *A61K 39/3955* (2013.01); *A61K 45/06* (2013.01)

(58) Field of Classification Search
CPC .......................... A61K 31/454; A61K 39/3955
See application file for complete search history.

(56) References Cited

U.S. PATENT DOCUMENTS 8,828,427 B2 * 9/2014 Tutino ................ A61K 9/4858
424/452
2008/0248046 A1 10/2008 Ni et al.

FOREIGN PATENT DOCUMENTS

| WO | 01/80884 A1 | 11/2001 | |
| WO | 02/064083 A2 | 8/2002 | |
| WO | 2010/135396 A2 | 11/2010 | |
| WO | WO 2010135396 A2 * | 11/2010 | ........... A61K 9/4858 |
| WO | 2014/071280 A1 | 5/2014 | |

OTHER PUBLICATIONS

Lacy et al. Blood, (2011), 118(11), p. 2970-2975, published Jun. 20, 2011.*
Li et al. PloS One (2013).*
Kotla et al. Journal of Hematology & Oncology (2009) 2:36.*
Anonymous, "Phase I trial of pomalidomide for patients with relapsed/refractory primary CNS lymphoma and patients with newly diagnosed or relapsed/refractory primary vitreoretinal lymphoma," Nov. 5, 2012, retrieved from the internet: URL:http//clinicaltrials.gov/archive/NCT01722305/2012_11_05, retrieved on Jun. 27, 2014, 16 pages.
Cox et al., "Lenalidomide for aggressive B-cell lymphoma involving the central nervous system," Am. J. Hematology, 86(11):957 (2011).
Gertz, "Pomalidomide and myeloma meningitis," Leuk. Lymphoma., 54(4):681-682 (2013).
Rubenstein et al., "Regression of refractory intraocular large B-cell lymphoma with lenalidomide monotherapy," J. Clin. Oncol., 29(20):e595-e597 (2011).

* cited by examiner

*Primary Examiner* — Yong Chu
(74) *Attorney, Agent, or Firm* — Jones Day

(57) ABSTRACT

Methods and compositions for treating, preventing or managing central nervous system cancers are disclosed. The methods encompass the administration of 4-amino-2-(2,6-dioxo-piperidine-3-yl)-isoindoline-1,3-dione, also known as Pomalidomide. Furthermore, provided herein are methods of treatment using this compound with chemotherapy, radiation therapy, hormonal therapy, biological therapy or immunotherapy. Pharmaceutical compositions and single unit dosage forms suitable for use in the methods provided herein are also disclosed.

27 Claims, 14 Drawing Sheets

A-1. Iba-1 stained macrophages

A-2. Contralateral Brain

A-3. Tumor

Figure 1:
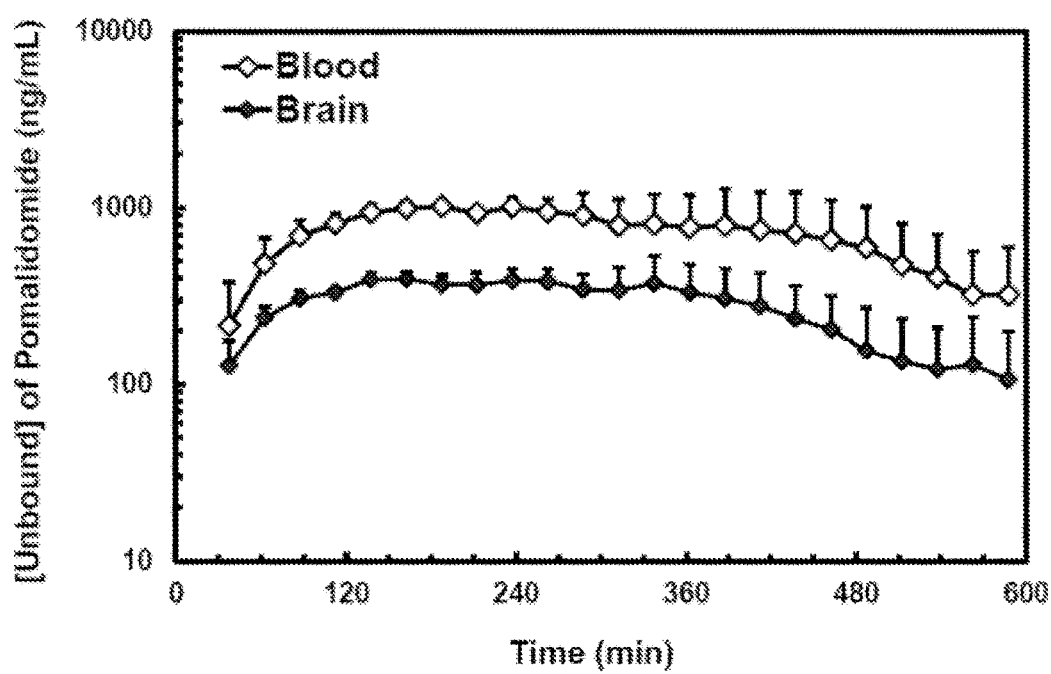

B-1.

B-2. iNOS stained cell count

B-3. Ym1 stained cell count

A. Raji CNS lymphoma model

B. OCI-LY10 CNS lymphoma model

Human monocyte-U937

A.

B.

C.

D.

A. Primary microglia cells

B. Human monocytes U937

Primary murine microglia cells

Primary murine peritoneal macrophages

A.

B.

C.

D.

A. Co-culture: Raji+Microglia

B. Triple-culture : Raji+Microglia+NK

METHODS AND COMPOSITIONS USING 4-AMINO-2-(2,6-DIOXO-PIPERIDINE-3-YL)-ISOINDOLINE-1,3-DIONE FOR TREATMENT AND MANAGEMENT OF CENTRAL NERVOUS SYSTEM CANCERS

This application is a national phase entry pursuant to 35 U.S.C. §371 of International Application No. PCT/US2014/032483, filed Apr. 1, 2014, which claims priority to U.S. Provisional Patent Application No. 61/807,605, filed Apr. 2, 2013, the entirety of each of which is hereby incorporated by reference.

1. FIELD

Provided herein are methods of treating, preventing and/or managing certain types of central nervous system cancers, and other diseases including, but not limited to, primary central nervous system lymphoma ("PCNSL"), primary vitreoretinal lymphoma ("PVRL"), intra-ocular lymphoma, central nervous system blastoid mantle cell lymphoma, central nervous system tumors, central nervous system solid tumors, central nervous system cancerous conditions, by the administration of 4-amino-2-(2,6-dioxo-piperidine-3-yl)-isoindoline-1,3-dione, alone or in combination with other therapeutics. In particular, provided herein are the use of specific combinations, or "cocktails," of drugs and other therapy, e.g., radiation to treat these specific cancers, including those refractory to conventional therapy. The field also relates to pharmaceutical compositions and dosing regimens.

Provided herein are the use of specific combinations or "cocktails" of 4-amino-2-(2,6-dioxo-piperidine-3-yl)-isoindoline-1,3-dione and other therapy, e.g., radiation or other chemotherapeutics, including but not limited to, anti-cancer agents, immunosuppressive agents, and anti-inflammatories such as steroids. The field also relates to pharmaceutical compositions and dosing regimens with said compound alone that is as a therapeutic.

2. BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and to distant sites (metastasis). Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Roitt, I., Brostoff, J. and Kale, D., *Immunology*, 17.1-17.12 (3rd ed., Mosby, St. Louis, Mo., 1993).

There is an enormous variety of cancers which are described in detail in the medical literature. Examples includes cancer of the blood, lung, colon, rectum, prostate, breast, brain, and intestine. The various forms of the cancers such as lymphomas are described in U.S. provisional application No. 60/380,842, filed May 17, 2002, the entireties of which are incorporated herein by reference (see, e.g., Section 2.2. Types of Cancers).

Many types of cancers are associated with new blood vessel formation, a process known as angiogenesis. Several of the mechanisms involved in tumor induced angiogenesis have been elucidated. The most direct of these mechanisms is the secretion by the tumor cells of cytokines with angiogenic properties. Examples of these cytokines include acidic and basic fibroblastic growth factor ("a,b FGF"), angiogenin, vascular endothelial growth factor ("VEGF"), and TNF-α. Alternatively, tumor cells can release angiogenic peptides through the production of proteases and the subsequent breakdown of the extracellular matrix where some cytokines are stored (e.g., bFGF). Angiogenesis can also be induced indirectly through the recruitment of inflammatory cells (particularly macrophages) and their subsequent release of angiogenic cytokines (e.g., TNF-α, bFGF).

Accordingly, compounds that can control angiogenesis or inhibit the production of certain cytokines, including TNF-α, may be useful in the treatment and prevention of various cancerous diseases and conditions.

Lymphoma is a heterogenous group of neoplasms arising in the reticuloendothelial and lymphatic systems. *The Merck Manual*, 955 (17$^{th}$ ed. 1999). Non-Hodgkin's lymphoma ("NHL") refers to malignant monoclonal proliferation of lymphoid cells in the immune system, including lymph nodes, bone marrow, spleen, liver and gastrointestinal ("GI") tract. *The Merck Manual*, at 958.

Mantle cell lymphoma ("MCL") is a distinct entity among the non-Hodgkin's lymphomas. Drach J.; et al., *Expert Review of Anticancer Therapy*, 2005, 5(3), pp. 477-485. In the International Lymphoma Classification Project, MCL accounted for 8% of all non-Hodgkin lymphomas. MCL is recognized in the Revised European-American Lymphoma and World Health Organization classifications as a distinct clinicopathologic entity. MCL was not recognized by previous lymphoma classification schemes; and it was frequently categorized as diffuse small-cleaved cell lymphoma by the International Working Formulation or centrocytic lymphoma by the Kiel classification. The Merck Manual, at 958-959.

MCL is a lymphoproliferative disorder derived from a subset of naive pregerminal center cells localized in primary follicles or in the mantle region of secondary follicles. MCL is characterized by a specific chromosomal translocation, the t(11; 14)(q13;q32). Drach J.; et al., *Expert Review of Anticancer Therapy*, 2005, 5(3), pp. 477-485. This translocation involves the immunoglobulin heavy-chain gene on chromosome 14 and the BCL1 locus on chromosome 11. Drach J.; et al., p 477. The molecular consequence of translocation is overexpression of the protein cyclin D1 (coded by the PRAD1 gene located close to the breakpoint). Id. Cyclin D1 plays a key role in cell cycle regulation and progression of cells from G1 phase to S phase by activation of cyclin-dependent kinases. Id.

NHL has been associated with viral infection (Ebstein-Barr virus, HIV, human T-lymphotropic virus type 1, human herpesvirus 6), environmental factors (pesticides, hair dyes), and primary and secondary immunodeficiency. No causative factor has been identified for MCL or for most patients with NHL of other types. MCL has poor clinical outcome and is an incurable lymphoma with limited therapeutic options for patients with relapsed or refractory disease. Drach J.; et al., p. 477.

Primary central nervous system lymphoma ("PCNSL") is most frequently a diffuse large B cell lymphoma ("DLBCL") confined to the central nervous system ("CNS") and carries a poor prognosis. Ferreri, A. J., *Blood*, 2011, 118, pp. 510-522. CNS tumor microenvironment plays an important role in the biology of CNS lymphoma. The standard therapy consists of high-dose methotrexate and high-dose ara-c with or without radiation. Although there has been an improvement in the survival due to these treatments, the prognosis of CNS lymphoma remains poor compared to systemic DLBCL. Id. Current therapeutic agents target lymphoma cells and have no significant impact on the tumor microenvironment. The blood brain barrier is a major obstacle for effective treatment of CNS lymphoma. Therefore, a tremendous demand exists for new methods, therapeutic agents, and compositions with better efficacy, excellent CNS penetration, and impact on the tumor microenvironment as well as lymphoma cells.

3. SUMMARY

Provided herein are methods and compositions for treating, preventing or managing certain types of cancer including lymphomas, primary and metastatic cancer, as well as cancers that are relapsed, refractory or resistant to conventional chemotherapy. In particular, methods herein encompass those for treating, preventing or managing various forms of cancer such as primary central nervous system lymphoma ("PCNSL"), primary vitreoretinal lymphoma ("PVRL"), intra-ocular lymphoma, central nervous system blastoid mantle cell lymphoma, central nervous system tumors, central nervous system solid tumors, central nervous system cancerous conditions, mantle cell lymphoma ("MCL"), lymphocytic lymphoma of intermediate differentiation, intermediate lymphocytic lymphoma ("ILL"), diffuse poorly differentiated lymphocytic lymphoma ("PDL"), centrocytic lymphoma, diffuse small-cleaved cell lymphoma ("DSCCL"), follicular lymphoma, and mantle zone lymphoma, including lymphomas that are relapsed, refractory or resistant.

The methods comprise administering to a patient in need of such treatment, prevention or management a therapeutically or prophylactically effective amount of 4-amino-2-(2,6-dioxo-piperidine-3-yl)-isoindoline-1,3-dione provided herein, or a pharmaceutically acceptable salt, solvate (e.g., hydrate), stereoisomer, clathrate, or prodrug thereof. In a preferred embodiment, 4-amino-2-(2,6-dioxo-piperidine-3-yl)-isoindoline-1,3-dione is used alone, that is without other chemotherapeutics.

In another embodiment, 4-amino-2-(2,6-dioxo-piperidine-3-yl)-isoindoline-1,3-dione is administered in combination with a therapy conventionally used to treat, prevent or manage cancer. Examples of such conventional therapies include, but are not limited to, surgery, chemotherapy, radiation therapy, hormonal therapy, biological therapy, immunotherapy and combinations thereof.

Provided herein are pharmaceutical compositions, single unit dosage forms, and dosing regimens which comprise 4-amino-2-(2,6-dioxo-piperidine-3-yl)-isoindoline-1,3-dione, or a pharmaceutically acceptable salt, solvate (e.g., hydrate), stereoisomer, clathrate, or prodrug thereof, and a second, or additional, active agent or ingredient. Second active agents or ingredients include specific combinations, or "cocktails," of drugs or therapy, or both.

4. BRIEF DESCRIPTION OF FIGURES

FIG. 1 shows unbound Blood and Brain Concentration-Time Profiles of Pomalidomide in Male CD-IGS Rats Following a Single p.o. Administration at 50 mg/kg (n=3).

Figure 2:
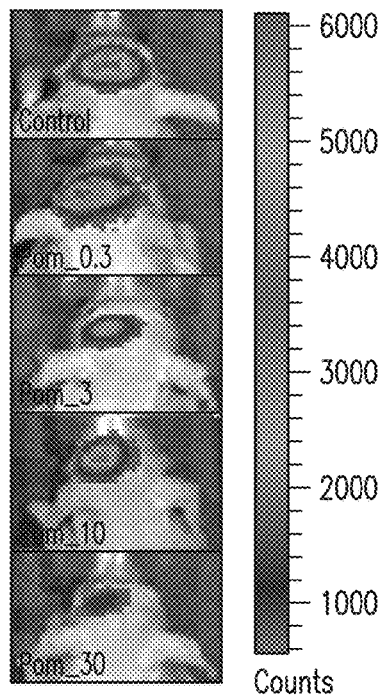
Figure 2:
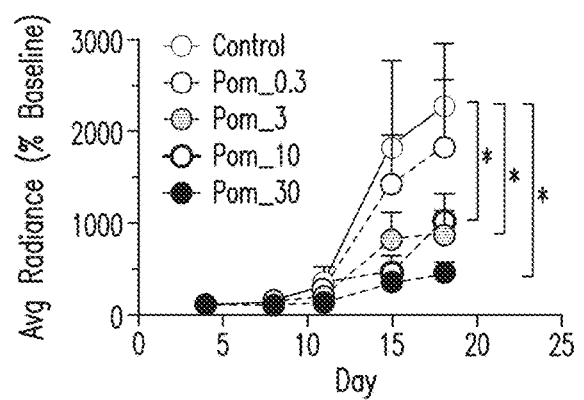
Figure 2:
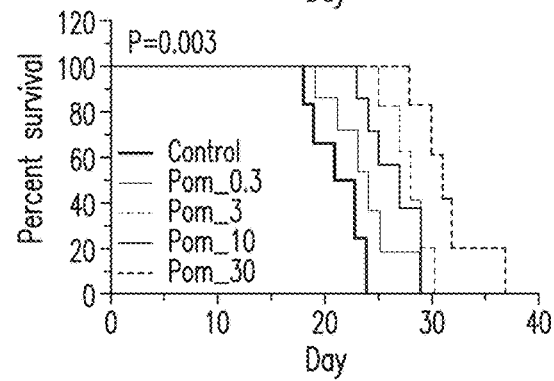
Figure 2:
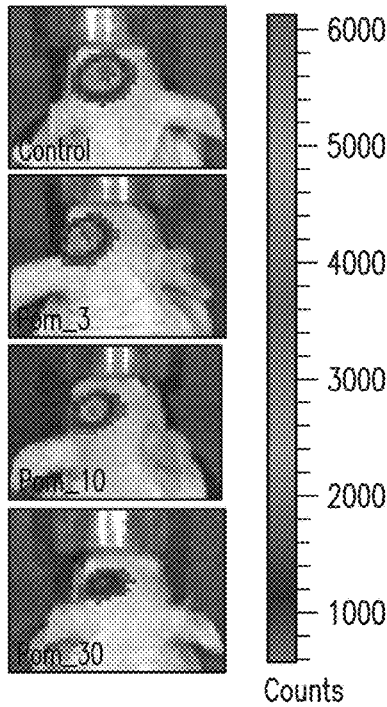
Figure 2:
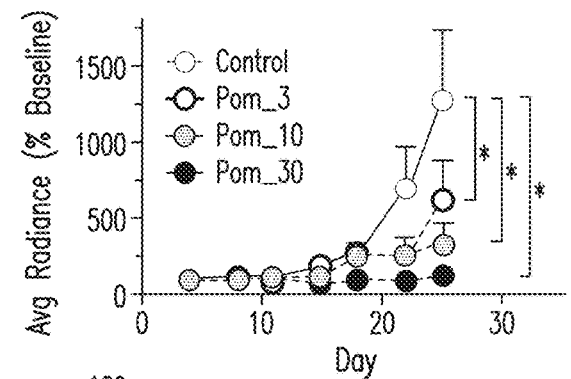
Figure 2:
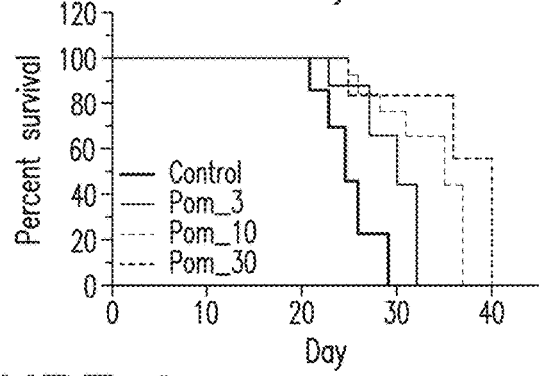

FIG. 2 shows that Pomalidomide ("POM") showed significant pre-clinical therapeutic activity with prolongation of survival in two in vivo CNS lymphoma models. Raji model: A-1, A-2 and A-3. OCI-LY10 model: B-1, B-2, and B-3. A-1. and B-1. Bioluminescence imaging of CNS lymphoma on day 18 post tumor implantation. A-2. and B-2. Luminescence signal of lymphoma growth post-intracerebral injection of 25,000 Raji cells or 1×105 OCI-LY10 cells. The data were shown as mean±SEM (average radiance % baseline) for n=8. In vivo tumor growth in Pom-3 mg/kg, Pom-10 mg/kg and Pom-30 mg/kg groups were significantly slower than that in the control group. *, P<0.05, as compared with control. A-3. and B-3. Kaplan-Meier analysis showed prolongation of survival with Pom_3 mg/kg, Pom_10 mg/kg and Pom-30 mg/kg treated groups (p<0.05, n=8).

Figure 3:
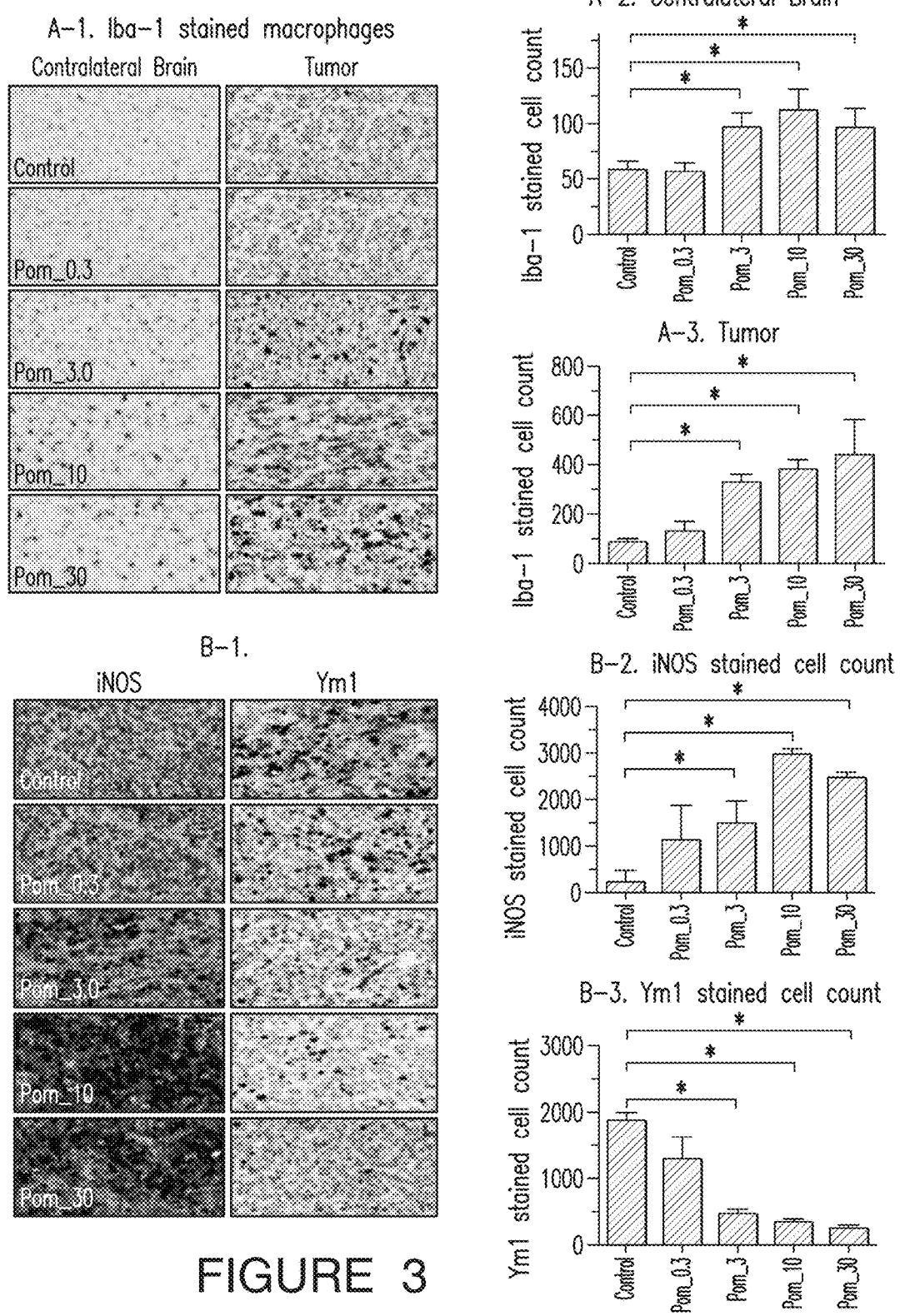

FIG. 3 shows Pomalidomide ("POM") had a major impact on macrophages in the CNS lymphoma microenvironment in Raji model. A. POM significantly increased brain macrophages. A-1. Iba-1 staining for brain macrophages in the contralateral brain and tumor. A-2. Quantitation of Iba-1 positive cells in the contra-lateral brain. A-3. Quantitation of Iba-1 positive cells in the tumor. B. Pomalidomide significantly decreased Ym1-expressing cells and increased iNOS-expressing cells in the intracranial lymphoma xenografts. B-1. iNOS and Ym1 staining macrophages in tumor. B-2. Quantitation of iNOS stained cells in the tumor. B-3. Quantitation of Ym1 stained cells in the tumor. (*, P<0.05 as compared with control group).

Figure 4:
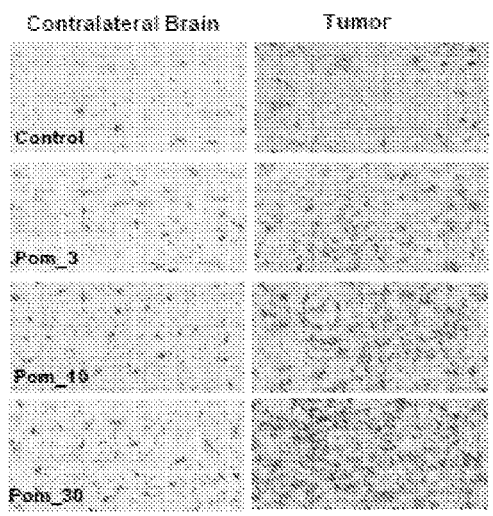
Figure 4:
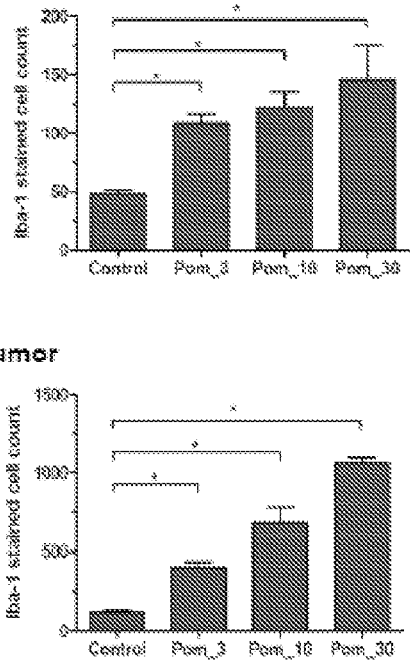
Figure 4:
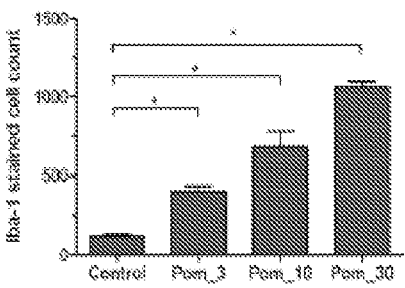
Figure 4:
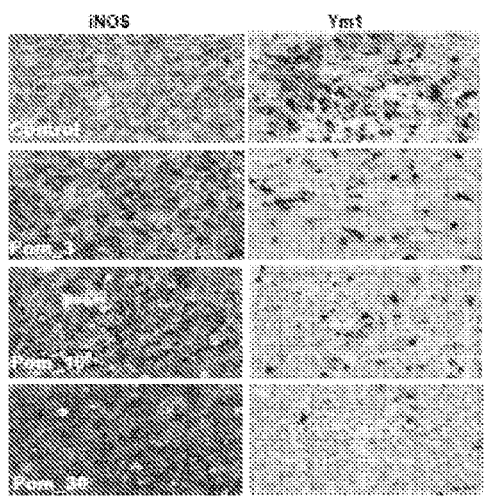
Figure 4:
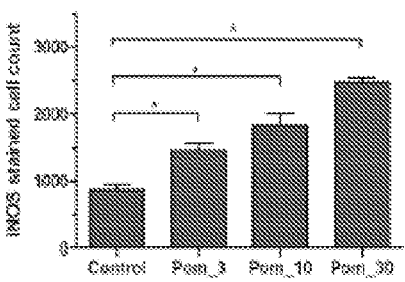
Figure 4:
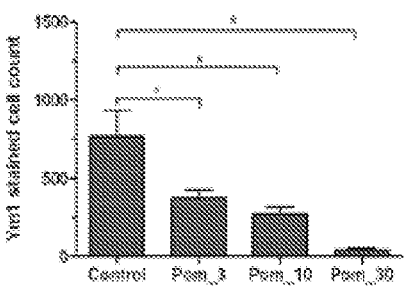

FIG. 4 shows Pomalidomide ("POM") had a major impact on macrophages in the CNS lymphoma microenvironment in OCI-LY10 model. A. Pomalidomide significantly increased brain macrophages. A-1. Iba-1 staining for brain macrophages in the contralateral brain and tumor. A-2. Quantitation of Iba-1 positive cells in the contra-lateral brain. A-3. Quantitation of Iba-1 positive cells in the tumor. B. Pomalidomide significantly decreased Ym1 expression and increased iNOS activity in the intracranial lymphoma xenografts. B-1. iNOS and Ym1 staining macrophages in tumor. B-2. Quantitation of iNOS stained cells in the tumor. B-3. Quantitation of Ym1 stained cells in the tumor. (*, P<0.05 as compared with control group).

Figure 5:
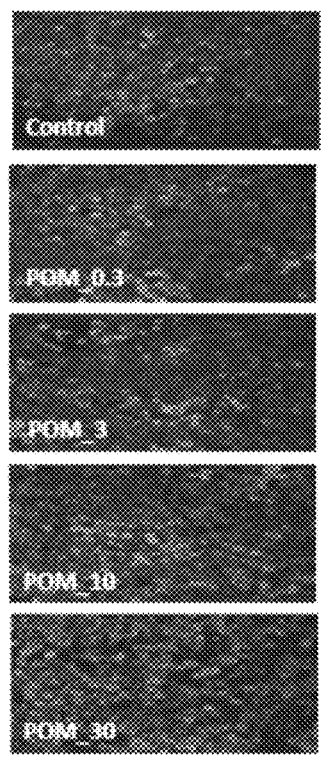
Figure 5:
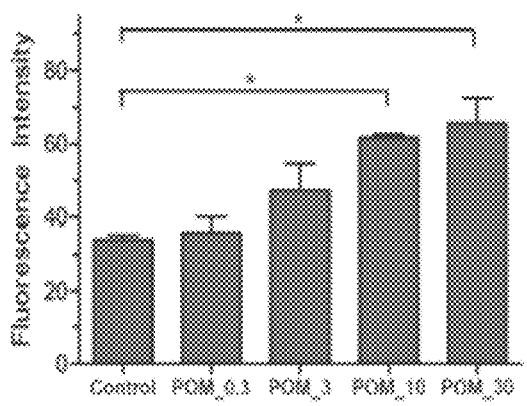
Figure 5:
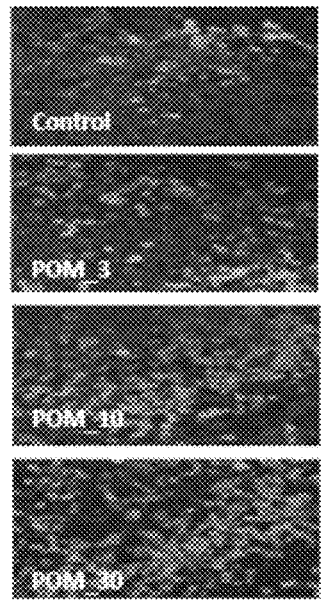
Figure 5:
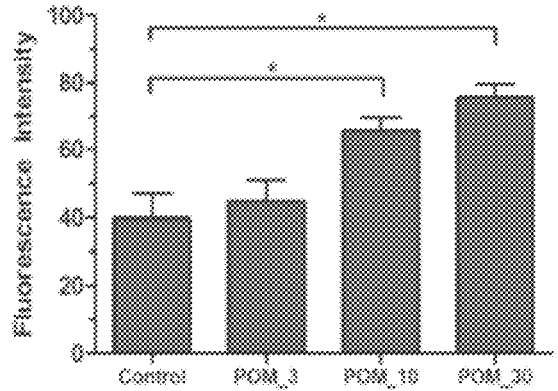

FIG. 5 shows Pomalidomide ("POM") significantly increased NK cells in CNS lymphoma microenvironment in the Raji and OCI-LY10 murine CNS lymphoma models. A-1. and B-1. POM significantly increased CD335 positive NK cells in CNS tumors. (original magnification ×200). A-2. and B-2. Fluorescence intensity of CD335 stained cells in the tumor. CD335 was used as a marker for NK cells. (*, P<0.05 as compared with control group).

Figure 6:
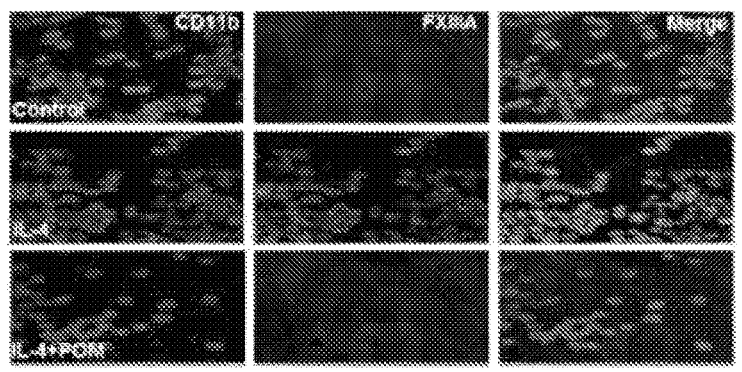
Figure 6:
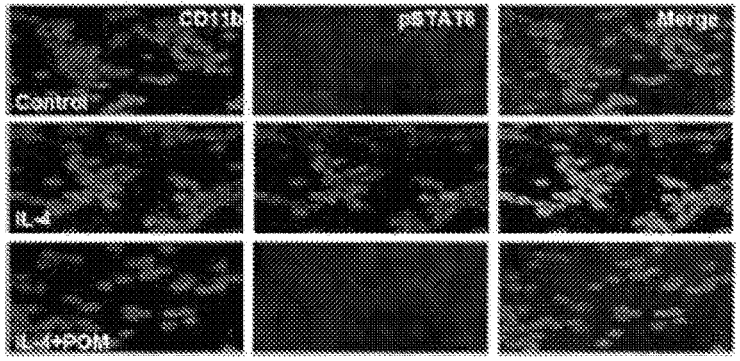
Figure 6:
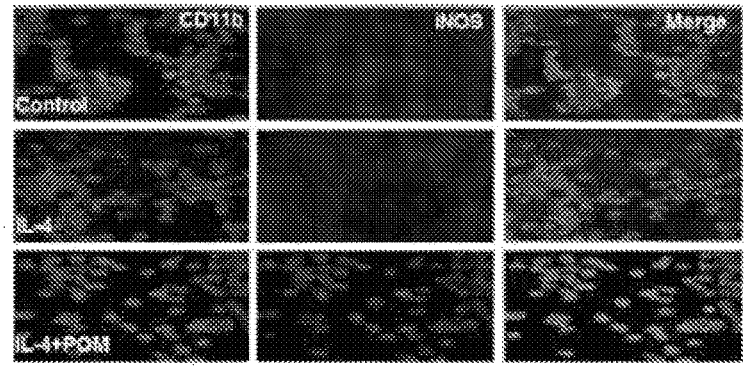
Figure 6:
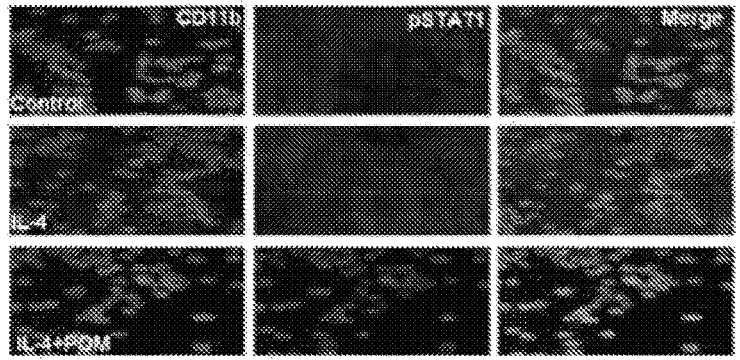

FIG. 6 shows Pomalidomide converted the polarization status of IL4-treated human monocyte U937 from M2 to M1. Pomalidomide converted the IL-4-induced M2 polarization of human monocytes as indicated by FXIII A and pSTAT6 expression to M1 polarization as indicated by iNOS and pSTAT1 expression. CD11b is a marker of human monocytes. Final original magnification, ×400 oil.

Figure 7:
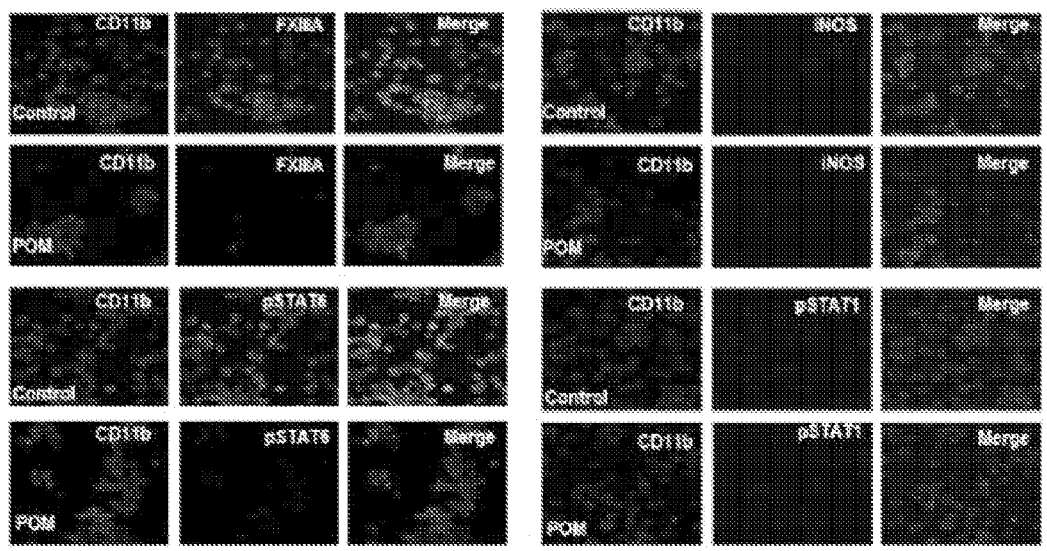
Figure 7:
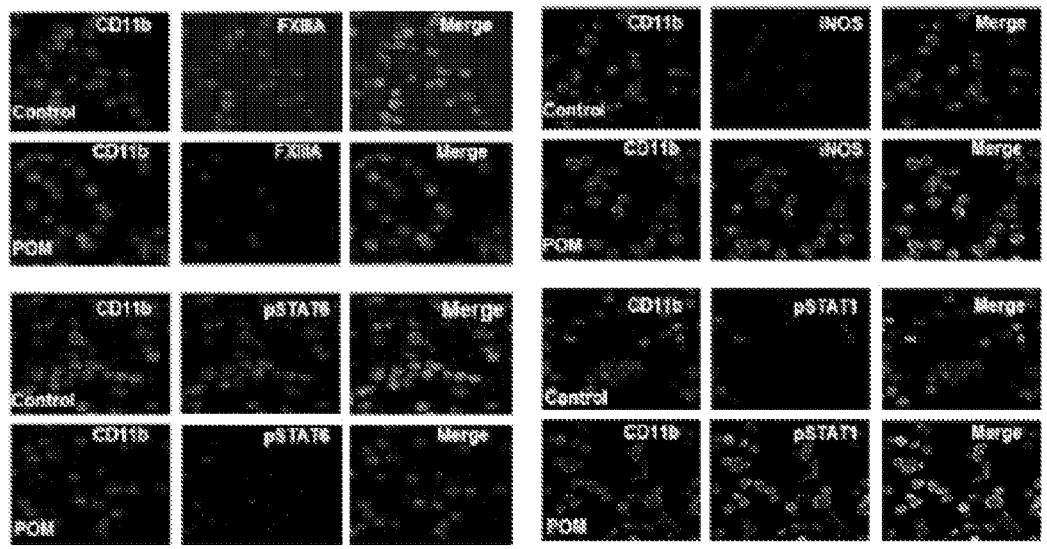

FIG. 7 shows Pomalidomide converted the polarization status of lymphoma (Raji)-associated macrophages from M2 to M1 in the presence of NK cells. U937 cells became M2-polarized as indicated by FXIIIA and pSTAT6 expression, when they were cocultured with Raji lymphoma cells. The M2 polarization of U937 cells was reversed by treatment with POM (A). U937 cells became M2 polarized when they were cocultured with Raji lymphoma cells and YTS NK cells. When the triple culture was treated with POM treatment, M1 polarization of U937 cells was detected, as indicated by iNOS and pSTAT1 expression (B). CD11b is a marker of human monocytes. Final original magnification, ×400 oil.

Figure 8:
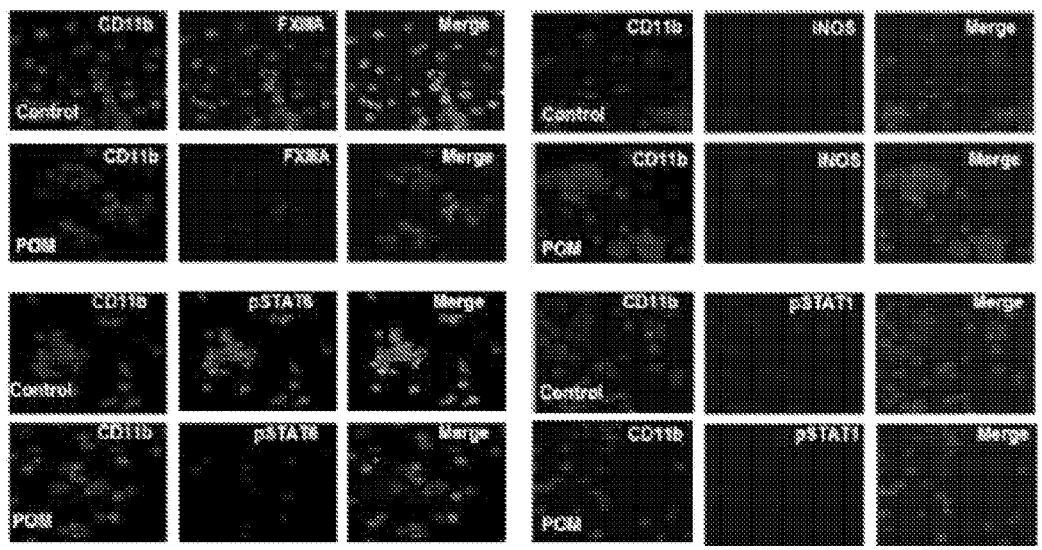
Figure 8:
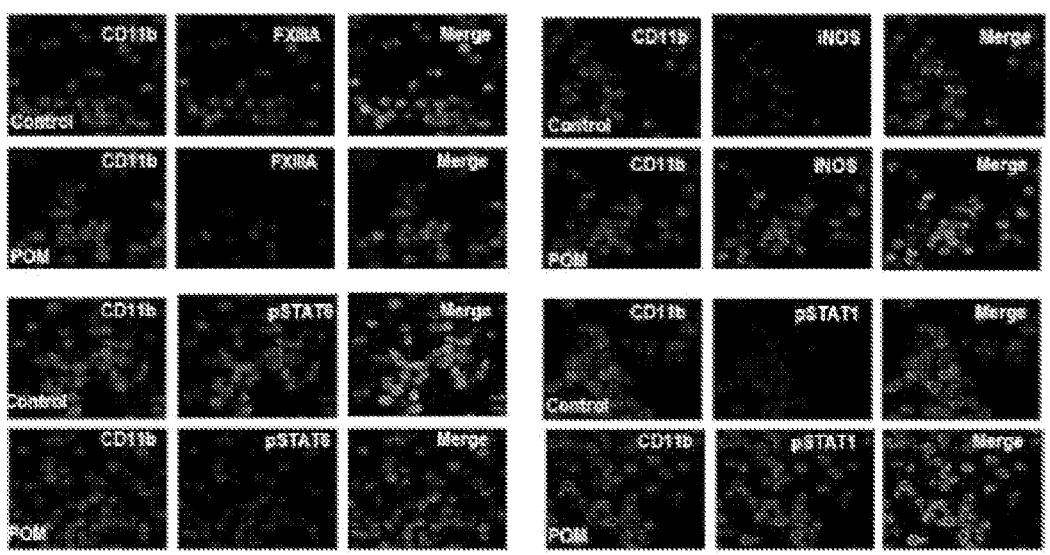

FIG. 8 shows Pomalidomide converted the polarization status of lymphoma (OCI-LY10)-associated macrophages from M2 to M1 in the presence of NK cells. U937 cells became M2-polarized as indicated by FXIIIA and pSTAT6 expression, when they were cocultured with OCI-LY10 lymphoma cells. The M2 polarization of U937 cells was reversed by treatment with POM (A). U937 cells became M2 polarized when they were cocultured with OCI-LY10 lymphoma cells and YTS NK cells. When the triple culture was treated with POM treatment, M1 polarization of U937 cells was detected, as indicated by iNOS and pSTAT1 expression (B). CD11b is a marker of human monocytes. Final original magnification, ×400 oil.

Figure 9:
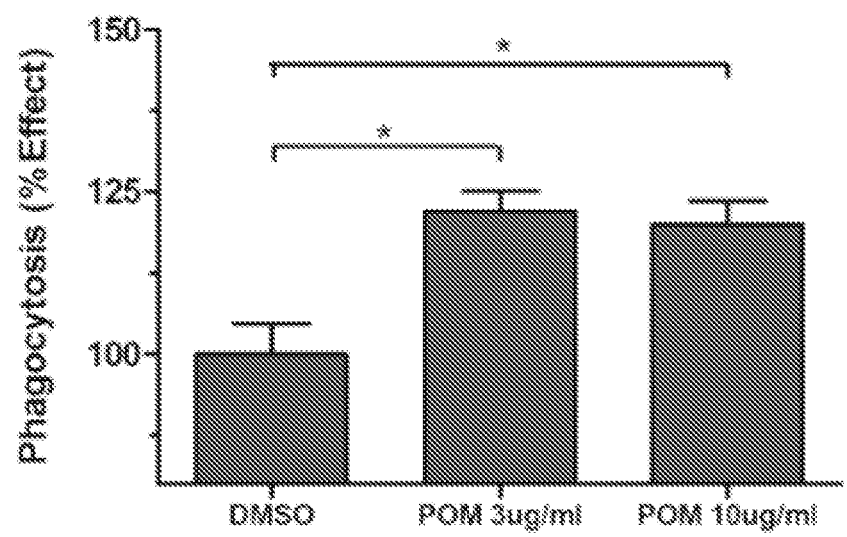
Figure 9:
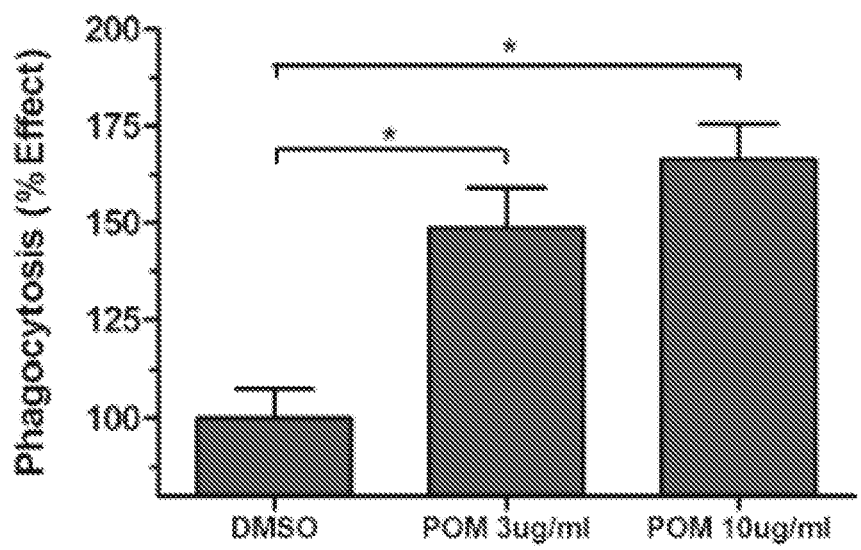

FIG. 9 shows Pomalidomide significantly increased the phagocytic activity of primary murine microglia cells (A) and human monocyte U937 cells (B). (*, P<0.05 as compared with control group).

Figure 10:
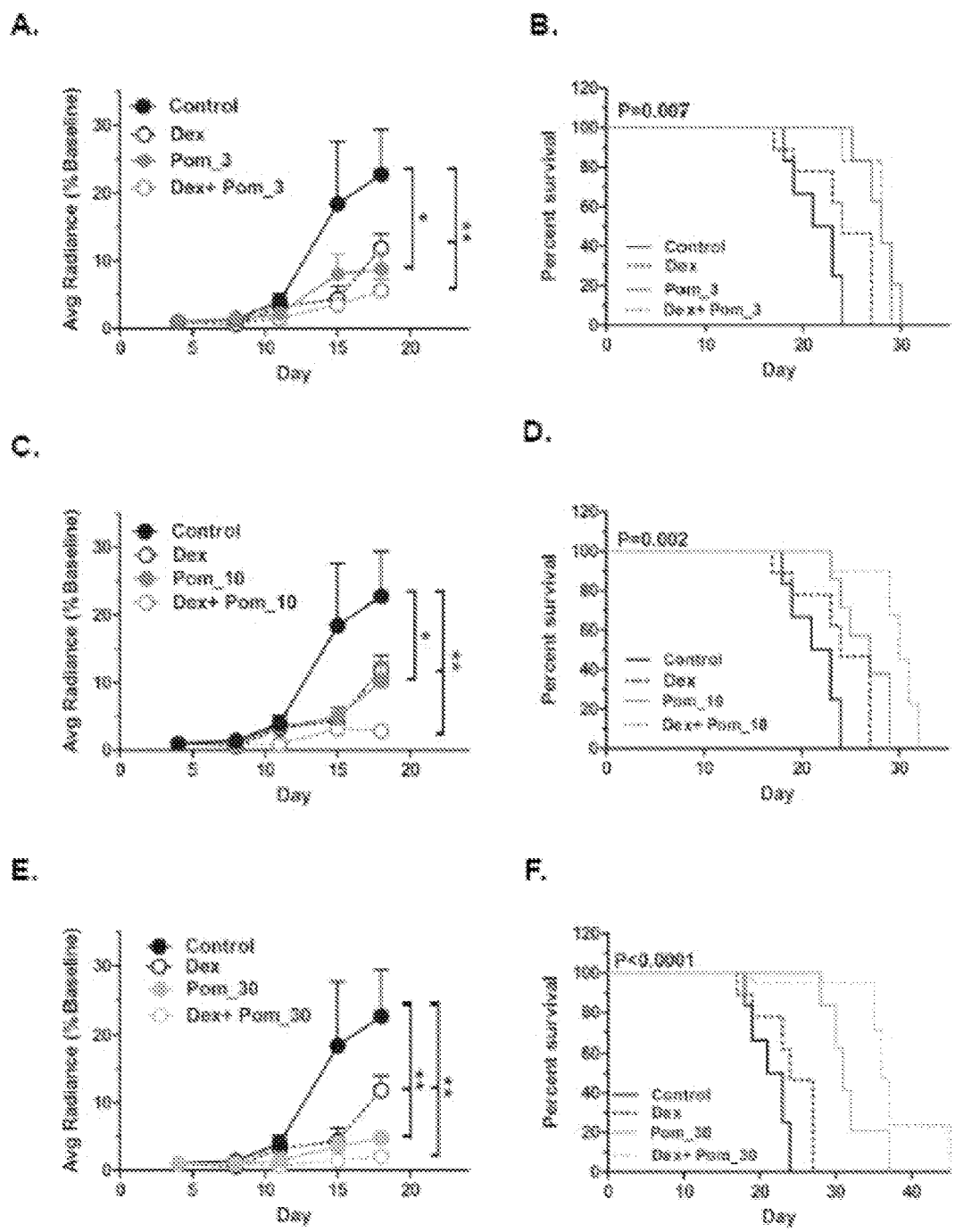

FIG. 10 shows that the addition of weekly Dexamethasone ("DEX") to Pomalidomide ("POM") led to further improvement in survival in Raji CNS lymphoma model. A. C. E. Luminescence signal of lymphoma growth on day 4, 8, 11, 15 and 18 post-intracerebral injection of 25,000 Raji cells. The data were shown as mean±SEM (average radiance) for n=8. *, P<0.05 as compared with control; , P<0.05, as compared with control and DEX;*, P<0.05, as compared with control, DEX alone and POM alone treatment group. B. D. F. Kaplan-Meier analysis shows prolongation of survival with DEX+POM_10 mg/kg and DEX+POM-30 mg/kg treated groups as compared with POM alone treated groups (p<0.05, n=8).

Figure 11:
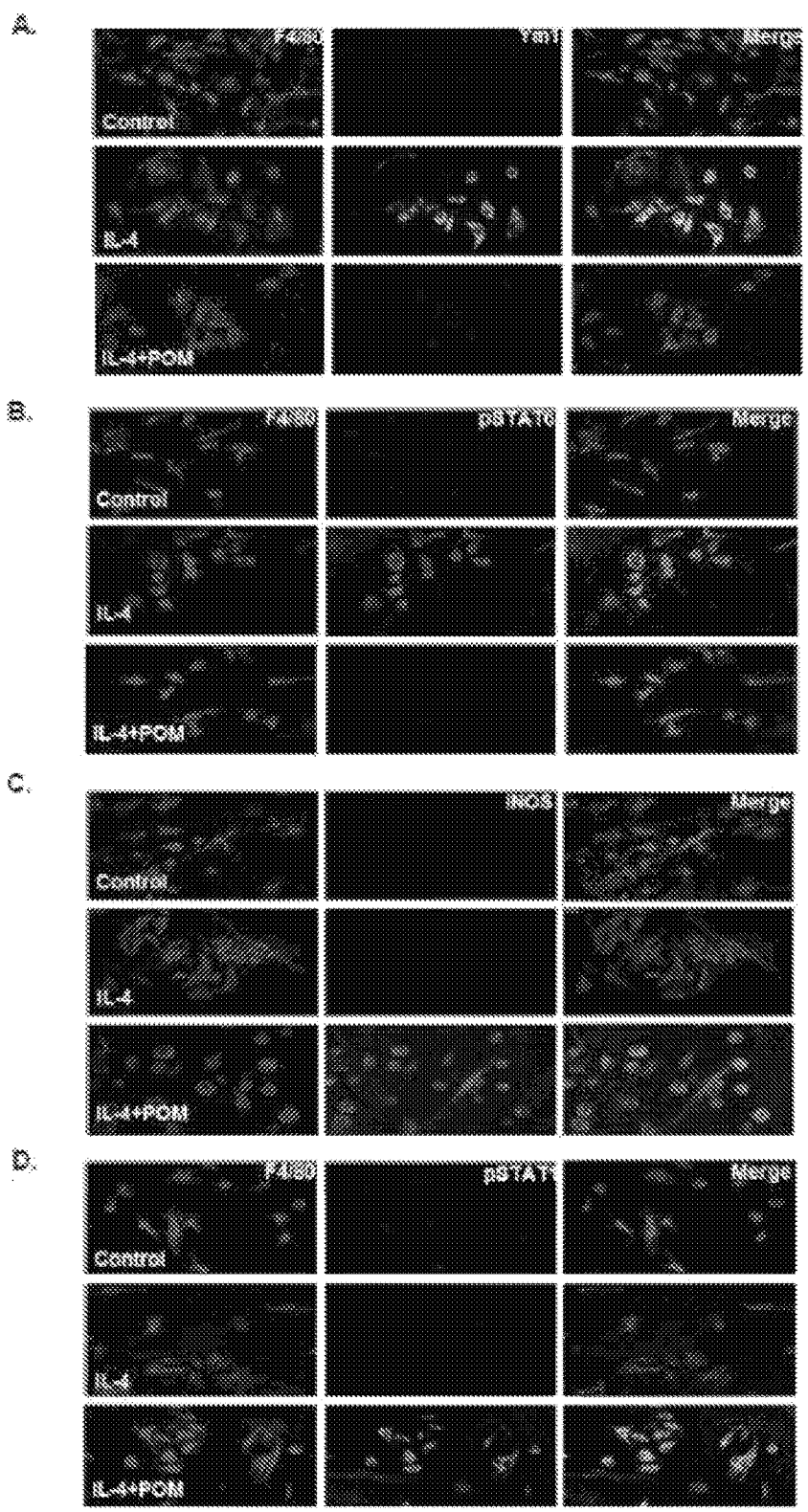

FIG. 11 shows Pomalidomide converted the polarization status of IL4-treated primary murine microglia cells from M2 to M1. Pomalidomide converted the IL-4-induced M2 polarization of microglia cells as indicated by FXIII A and pSTAT6 expression to M1 polarization as indicated by iNOS and pSTAT1 expression. CD11b is a marker of human monocytes. Final original magnification, ×400 oil.

Figure 12:
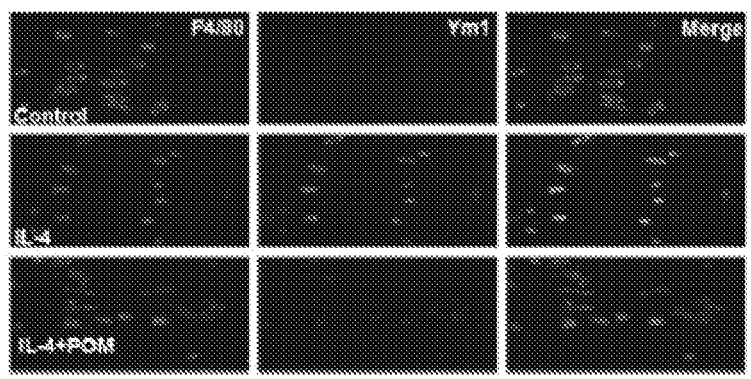
Figure 12:
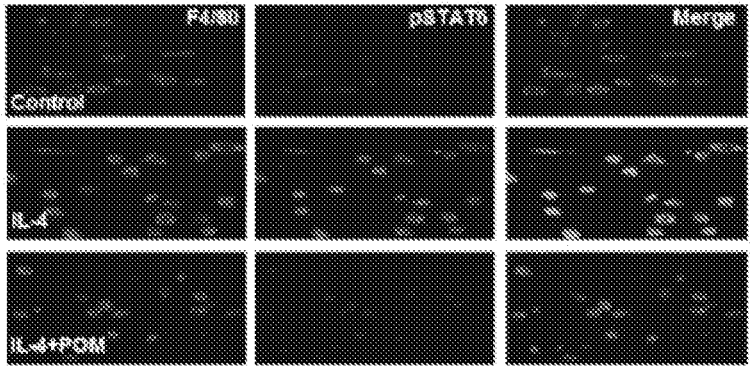
Figure 12:
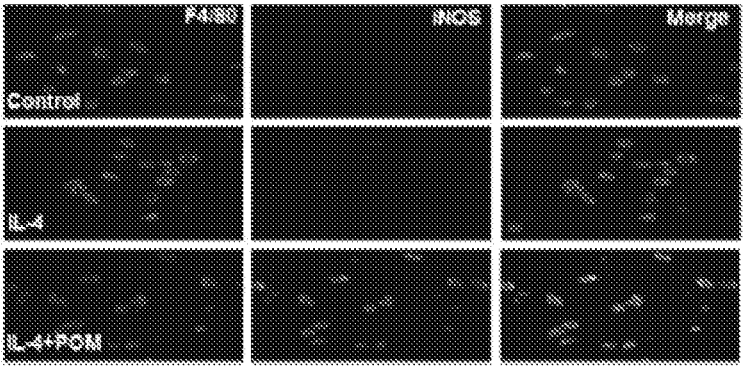
Figure 12:
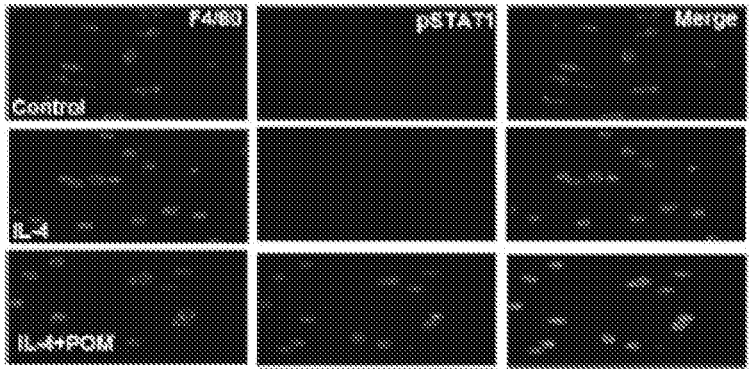

FIG. 12 shows Pomalidomide converted the polarization status of IL4-treated primary murine peritoneal macrophages from M2 to M1. Pomalidomide converted the IL-4-induced M2 polarization of macrophages as indicated by FXIII A and pSTAT6 expression to M1 polarization as indicated by iNOS and pSTAT1 expression. CD11b is a marker of human monocytes. Final original magnification, ×400 oil.

Figure 13:
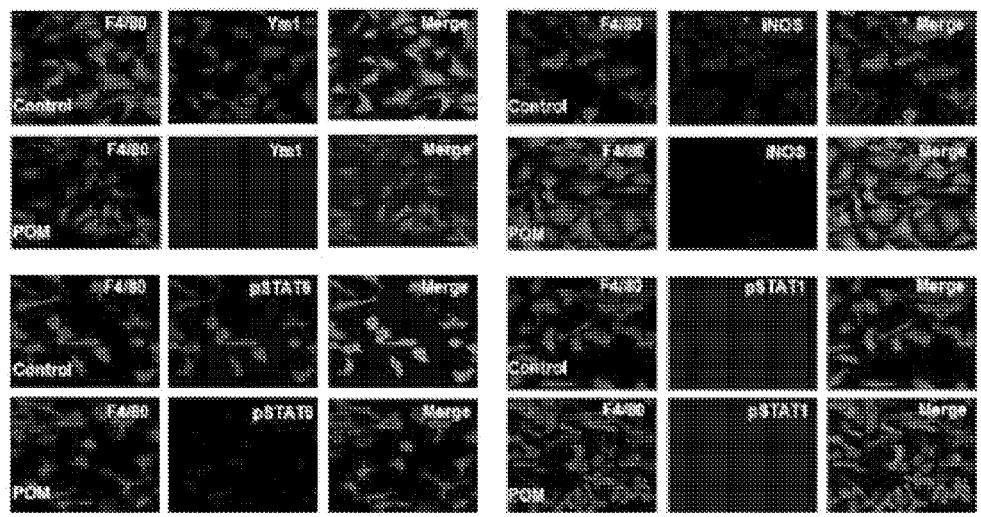
Figure 13:
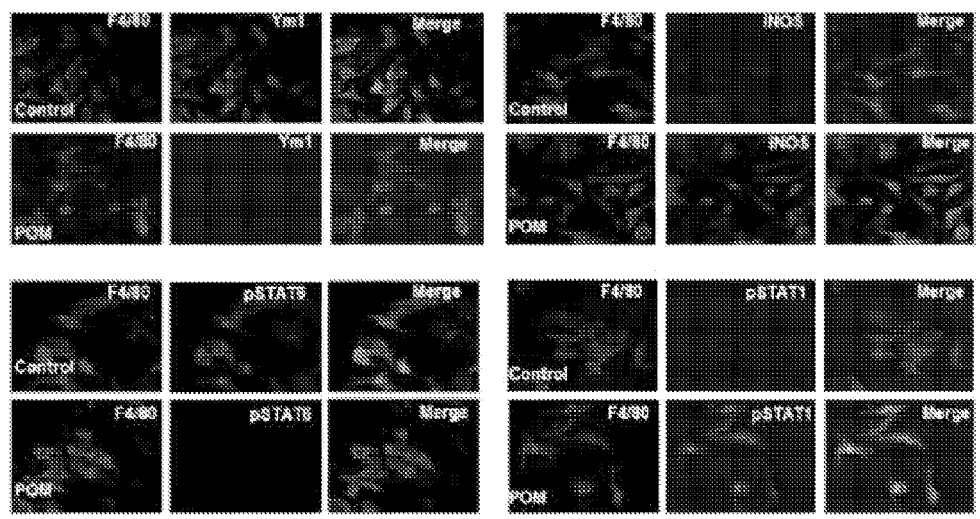

FIG. 13 shows Pomalidomide converted the polarization status of lymphoma (Raji)-associated primary murine microglia cells from M2 to M1 in the presence of primary murine NK cells. Microglia cells became M2-polarized as indicated by FXIIIA and pSTAT6 expression, when they were cocultured with Raji lymphoma cells. Their M2 polarization was reversed by treatment with POM (A). They became M2 polarized when they were cocultured with Raji lymphoma cells and primary NK cells. When the triple culture was treated with POM treatment, M1 polarization of microglia cells was detected, as indicated by iNOS and pSTAT1 expression (B). F4/80 is a marker of murine microglia cells. Final original magnification, ×400 oil.

Figure 14:
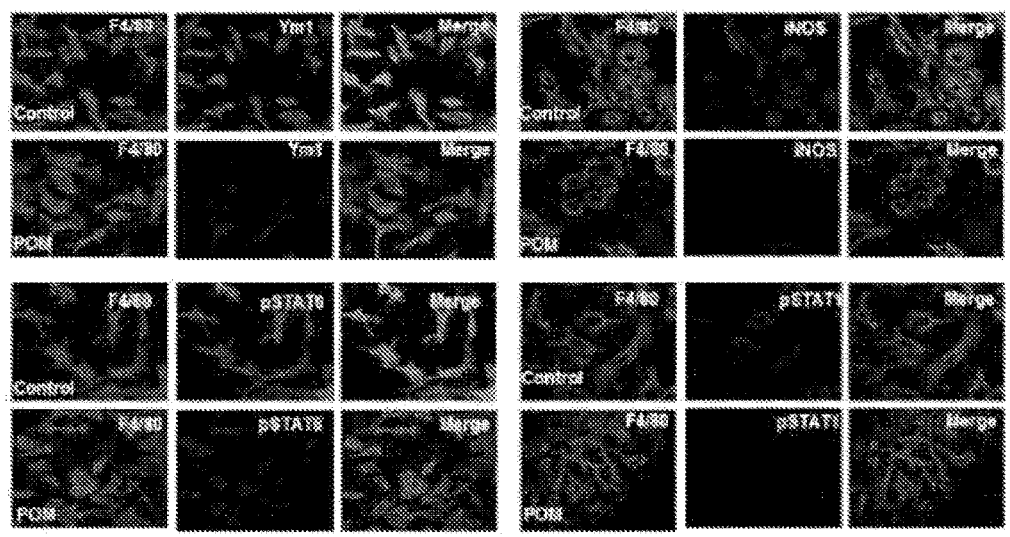
Figure 14:
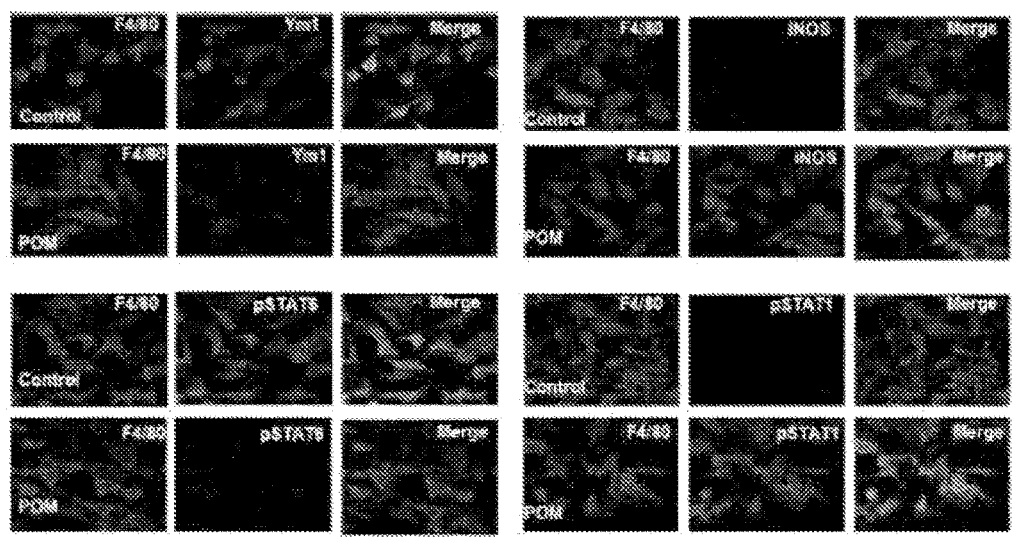

FIG. 14 shows Pomalidomide converted the polarization status of lymphoma (OCI-LY10)-associated primary murine microglia cells from M2 to M1 in the presence of primary murine NK cells. Microglia cells became M2-polarized as indicated by FXIIIA and pSTAT6 expression, when they were cocultured with OCI-LY10 lymphoma cells. Their M2 polarization was reversed by treatment with POM (A). They became M2 polarized when they were cocultured with OCI-LY10 lymphoma cells and primary NK cells. When the triple culture was treated with POM treatment, M1 polarization of microglia cells was detected, as indicated by iNOS and pSTAT1 expression (B). F4/80 is a marker of murine microglia cells. Final original magnification, ×400 oil.

5. DETAILED DESCRIPTION

A first embodiment encompasses methods of treating, managing, or preventing cancer which comprises administering to a patient in need of such treatment, management or prevention a therapeutically or prophylactically effective amount of 4-amino-2-(2,6-dioxo-piperidine-3-yl)-isoindoline-1,3-dione provided herein, or a pharmaceutically acceptable salt, solvate (e.g., hydrate), stereoisomer, clathrate, or prodrug thereof.

In particular, methods encompass those for treating, preventing or managing various forms of cancer, including but not limited to primary central nervous system lymphoma ("PCNSL"), primary vitreoretinal lymphoma ("PVRL"), intra-ocular lymphoma, central nervous system blastoid mantle cell lymphoma, central nervous system tumors, central nervous system solid tumors, central nervous system cancerous conditions, mantle cell lymphoma ("MCL"), lymphocytic lymphoma of intermediate differentiation, intermediate lymphocytic lymphoma ("ILL"), diffuse poorly differentiated lymphocytic lymphoma ("PDL"), centrocytic lymphoma, diffuse small-cleaved cell lymphoma ("DSCCL"), follicular lymphoma, mantle zone lymphoma, and any type of the mantle cell lymphomas that can be seen under the microscope (nodular, diffuse, blastic and mantle zone lymphoma). In one embodiment, the cancer is refractory, relapsed, or is resistant to chemotherapy other than 4-amino-2-(2,6-dioxo-piperidine-3-yl)-isoindoline-1,3-dione.

In a separate and distinct embodiment, 4-amino-2-(2,6-dioxo-piperidine-3-yl)-isoindoline-1,3-dione is administered in combination with another drug ("second active agent or ingredient") or another therapy for treating, managing, or preventing cancer. Second active agents include small molecules and large molecules (e.g., proteins and antibodies), examples of which are provided herein, as well as stem cells or cord blood. Methods, or therapies, that can be used in combination with the administration of 4-amino-2-(2,6-dioxo-piperidine-3-yl)-isoindoline-1,3-dione provided herein include, but are not limited to, surgery, blood transfusions, immunotherapy, biological therapy, radiation therapy, and other non-drug based therapies presently used to treat, prevent or manage cancer.

Another embodiment encompasses methods of treating, managing or preventing diseases and disorders other than cancer that are characterized by undesired angiogenesis. These methods comprise the administration of a therapeutically or prophylactically effective amount of 4-amino-2-(2,6-dioxo-piperidine-3-yl)-isoindoline-1,3-dione, or a pharmaceutically acceptable salt, solvate, hydrate, stereoisomer, clathrate, or prodrug thereof.

Provided herein are pharmaceutical compositions (e.g., single unit dosage forms) that can be used in methods disclosed herein. Particular pharmaceutical compositions comprise 4-amino-2-(2,6-dioxo-piperidine-3-yl)-isoindoline-1,3-dione, or a pharmaceutically acceptable salt, solvate (e.g., hydrate), stereoisomer, clathrate, or prodrug thereof, and a second active agent or ingredient.

5.1 Pomalidomide

Pomalidomide (also known as Pomalyst®), which was previously referred to as CC-4047, and has a chemical name of 4-amino-2-(2,6-dioxo-piperidine-3-yl)isoindoline-1,3-dione. Pomalidomide is a compound that inhibits, for example, LPS induced monocyte TNFα, IL-1β, IL-12, IL-6, MIP-1, MCP-1, GM-CSF, G-CSF, and COX-2 production, and may be used in treating various disorders. See, e.g., U.S. Pat. Nos. 5,635,517, 6,316,471, 6,476,052, 7,393,863, 7,629,360, and 7,863,297; and U.S. Patent Application Publication Nos. 2005/0143420, 2006/0166932, 2006/0188475, 2007/0048327, 2007/0066512, 2007/0155791, 2008/0051431, 2008/0317708, 2009/0087407, 2009/0088410, 2009/01317385, 2009/0148853, 2009/0232776, 2009/0232796, 2010/0098657, 2010/0099711, and 2011/0184025, the entireties of which are incorporated herein by reference. The compound is also known to co-stimulate the activation of T-cells. Pomalidomide has direct anti-myeloma tumoricidal activity, immunomodulatory activities and inhibits stromal cell support for multiple myeloma tumor cell growth. Specifically, pomalidomide inhibits proliferation and induces apoptosis of hematopoietic tumor cells. Id. Additionally, Pomalidomide inhibits the proliferation of lenalidomide-resistant multiple myeloma cell lines and synergizes with dexamethasone in both lenalidomide-sensitive and lenalidomide-resistant cell lines to induce tumor cell apoptosis. Pomalidomide enhances T cell- and natural killer ("NK") cell-mediated immunity, and inhibits production of pro-inflammatory cytokines (e.g., TNF-α and IL-6) by monocytes. Pomalidomide also inhibits angiogenesis by blocking the migration and adhesion of endothelial cells. Due to its diversified pharmacological properties, Pomalidomide is useful in treating, preventing, and/or managing various diseases or disorders.

Pomalidomide and methods of synthesizing the compound are described, e.g., in U.S. Pat. Nos. 5,635,517, 6,335,349, 6,316,471, 6,476,052, 7,041,680, 7,709,502, and 7,994,327; and U.S. Patent Application Publication Nos. 2006/0178402 and 2011/0224440; the entireties of which are incorporated herein by reference.

In the most preferred embodiment, 4-amino-2-(2,6-dioxopiperidine-3-yl)-isoindoline-1,3-dione has the following chemical structure:

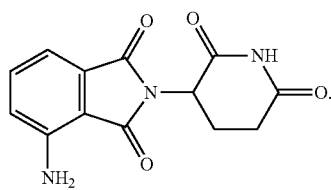 [SMILES: Nc1cccc2c1C(=O)N(C1CCC(=O)NC1=O)C2=O]

As used herein, and unless otherwise indicated, the compound referred to herein as "Pomalidomide," "CC-4047," "4-amino-2-(2,6-dioxo-piperidine-3-yl)-isoindoline-1,3-dione," or "POM" may be used herein to refer to, but not limited to, either a free base, pharmaceutically acceptable salt, solvate, hydrate, polymorph, isotopologue, deuterated derivative, co-crystal, prodrug, stereoisomer, racemate, enantiomer, and the like.

Unless otherwise specified, the terms "solid form," "solid forms," and related terms, when used herein to refer to Pomalidomide, refer to a physical form comprising Pomalidomide, which is not predominantly in a liquid or a gaseous state. As used herein, the terms "solid form" and "solid forms" encompass semi-solids. Solid forms may be crystalline, amorphous, partially crystalline, partially amorphous, or mixtures of forms. A "single-component" solid form comprising Pomalidomide consists essentially of Pomalidomide. A "multiple-component" solid form comprising Pomalidomide comprises a significant quantity of one or more additional species, such as ions and/or molecules, within the solid form. For example, in particular embodiments, a crystalline multiple-component solid form comprising Pomalidomide further comprises one or more species non-covalently bonded at regular positions in the crystal lattice.

Unless otherwise specified, the term "crystalline" and related terms used herein, when used to describe a substance, component, product, or form, mean that the substance, component, product, or form is substantially crystalline, for example, as determined by X-ray diffraction. (see, e.g., Remington's Pharmaceutical Sciences, 18th ed., Mack Publishing, Easton Pa., 173 (1990); The United States Pharmacopeia, 23rd ed., 1843-1844 (1995)).

Unless otherwise specified, the term "crystal form," "crystal forms," and related terms herein refer to crystalline modifications comprising a given substance, including single-component crystal forms and multiple-component crystal forms, and including, but not limited to, polymorphs, solvates, hydrates, co-crystals, other molecular complexes, salts, solvates of salts, hydrates of salts, co-crystals of salts, and other molecular complexes of salts, and polymorphs thereof. In some embodiments, a crystal form of a substance may be substantially free of amorphous forms and/or other crystal forms. In other embodiments, a crystal form of a substance may contain less than about 1%, 2%, 3%, 4%, 5%, 10%, 15%, 20%, 25%, 30%, 35%, 40%, 45%, or 50% of one or more amorphous form(s) and/or other crystal form(s) on a weight basis. Crystal forms of a substance may be obtained by a number of methods. Such methods include, but are not limited to, melt recrystallization, melt cooling, solvent recrystallization, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid evaporation, rapid cooling, slow cooling, vapor diffusion, sublimation, grinding, and solvent-drop grinding.

Unless otherwise specified, the terms "polymorph," "polymorphic form," "polymorphs," "polymorphic forms," and related terms herein refer to two or more crystal forms that consist essentially of the same molecule, molecules or ions. Different polymorphs may have different physical properties, such as, for example, melting temperatures, heats of fusion, solubilities, dissolution rates, and/or vibrational spectra as a result of a different arrangement or conformation of the molecules or ions in the crystal lattice. The differences in physical properties exhibited by polymorphs may affect pharmaceutical parameters, such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to thermodynamically a more stable polymorph) or both (e.g., tablets of one polymorph are more susceptible to breakdown at high humidity). As a result of solubility/dissolution differences, in the extreme case, some polymorphic transitions may result in lack of potency or, at the other extreme, toxicity. In addition, the physical properties of the crystal may be important in processing; for example, one polymorph might be more likely to form solvates or might be difficult to filter and wash free of impurities (e.g., particle shape and size distribution might be different between polymorphs). In exemplary embodiments, provided herein are solid forms of Pomalidomide, as disclosed in International Application No. PCT/US2013/026662, filed Feb. 19, 2013 and U.S. Provisional Application No. 61/805,444, filed Mar. 26, 2013, which are incorporated by reference herein in their entirety.

Unless otherwise specified, the term "cocrystal" or "co-crystal," as used herein, refers to a crystalline material comprised of two or more non-volative compounds bond together in a crystal lattice by non-covalent interactions.

Unless otherwise specified, the term "pharmaceutical co-crystal" or "co-crystal" of an active pharmaceutical ingredient ("API"), as used herein, refers to a crystalline material comprised of an API and one or more non-volative compound(s) (refereed herein as a coformer). The API and the coformer interact through non-covalent forces in a crystal lattice. In exemplary embodiments, provided herein are co-crystals of Pomalidomide, as disclosed in U.S. Provisional Application No. 61/805,444, filed Mar. 26, 2013, which is incorporated by reference herein in its entirety. In one embodiment, provided herein are solid forms (e.g., co-crystals) of Pomalidomide.

Unless otherwise specified, the term "amorphous," "amorphous form," and related terms used herein mean that the substance, component, or product referred to is not substantially crystalline as determined by X-ray diffraction. In certain embodiments, an amorphous form of a substance may be substantially free of crystal forms. In other embodiments, an amorphous form of a substance may contain less than about 1%, 2%, 3%, 4%, 5%, 10%, 15%, 20%, 25%, 30%, 35%, 40%, 45% or 50% of one or more crystal forms on a weight basis. In other embodiments, an amorphous form of a substance may comprise additional components or ingredients (for example, an additive, a polymer, or an excipient that may serve to further stabilize the amorphous form). In some embodiments, amorphous form may be a solid solution. Amorphous forms of a substance can be obtained by a number of methods. Such methods include, but are not limited to, heating, melt cooling, rapid melt cooling, solvent evaporation, rapid solvent evaporation, desolvation, sublimation, grinding, ball-milling, cryo-grinding, spray drying, and freeze drying.

The compounds provide herein may also contain an unnatural proportion of an atomic isotope at one or more of the atoms that constitute such a compound. For example, the compound may be radiolabeled with radioactive isotopes, such as for example tritium ($^{3}$H), iodine-125 ($^{125}$I) sulfur-35 ($^{35}$S), or carbon-14 ($^{14}$C). Radiolabeled compounds are useful as therapeutic agents, e.g., cancer therapeutic agents, research reagents, e.g., binding assay reagents, and diagnostic agents, e.g., in vivo imaging agents. All isotopic variations of the compounds provided herein, whether radioactive or not, are intended to be encompassed herein. In certain embodiments, a compound provided herein contains unnatural proportion(s) of one or more isotopes, including, but not limited to, hydrogen ($^{1}$H), deuterium ($^{2}$H), tritium ($^{3}$H), carbon-11 ($^{11}$C), carbon-12 ($^{12}$C), carbon-13 ($^{13}$C), carbon-14 ($^{14}$C), nitrogen-13 ($^{13}$N), nitrogen-14 ($^{14}$N), nitrogen-15 ($^{15}$N), oxygen-14 ($^{14}$O), oxygen-15 ($^{15}$O), oxygen-16 ($^{16}$O), oxygen-17 ($^{17}$O), oxygen-18 ($^{18}$O), fluorine-17 ($^{17}$F), fluorine-18 ($^{18}$F), phosphorus-31 ($^{31}$P), phosphorus-32 ($^{32}$P), phosphorus-33 ($^{33}$P), sulfur-32 ($^{32}$S), sulfur-33 ($^{33}$S), sulfur-34 ($^{34}$S), sulfur-35 ($^{35}$S), sulfur-36 ($^{36}$S), chlorine-35 ($^{35}$Cl), chlorine-36 ($^{36}$Cl), chlorine-37 ($^{37}$Cl), bromine-79 ($^{79}$Br), bromine-81 ($^{81}$Br), iodine-123 ($^{123}$I), iodine-125 ($^{125}$I), iodine-127 ($^{127}$I), iodine-129 ($^{129}$I), and iodine-131 ($^{131}$I). In certain embodiments, a compound provided herein contains unnatural proportion(s) of one or more isotopes in a stable form, that is, non-radioactive, including, but not limited to, hydrogen ($^{1}$H), deuterium ($^{2}$H), carbon-12 ($^{12}$C), carbon-13 ($^{13}$C), nitrogen-14 ($^{14}$N), nitrogen-15 ($^{15}$N), oxygen-16 ($^{16}$O), oxygen-17 ($^{17}$O), oxygen-18 fluorine-17 ($^{17}$F), phosphorus-31 ($^{31}$P), sulfur-32 ($^{32}$S), sulfur-33 ($^{33}$S), sulfur-34 ($^{34}$S), sulfur-36 ($^{36}$S), chlorine-35 ($^{35}$Cl), chlorine-37 ($^{37}$Cl), bromine-79 ($^{79}$Br), bromine-81 ($^{81}$Br), and iodine-127 ($^{127}$I). In certain embodiments, a compound provided herein contains unnatural proportion(s) of one or more isotopes in an unstable form, that is, radioactive, including, but not limited to, tritium ($^{3}$H), carbon-11 ($^{11}$C), carbon-14 ($^{14}$C), nitrogen-13 ($^{13}$N), oxygen-14 ($^{14}$O), oxygen-15 ($^{15}$O), fluorine-18 ($^{18}$F), phosphorus-32 ($^{32}$P), phosphorus-33 ($^{33}$P), sulfur-35 ($^{35}$S), chlorine-36 ($^{36}$Cl), iodine-123 ($^{123}$I), iodine-125 ($^{125}$I), iodine-129 ($^{129}$I), and iodine-131 ($^{131}$I). In certain embodiments, in a compound as provided herein, any hydrogen can be $^{2}$H, for example, or any carbon can be $^{13}$C, for example, or any nitrogen can be $^{15}$N, for example, or any oxygen can be $^{18}$O, for example, where feasible according to the judgment of one of skill. In certain embodiments, a compound provided herein contains unnatural proportions of deuterium ("D"). In exemplary embodiments, provided herein are isotopologues of Pomalidomide, as disclosed in U.S. Provisional Application No. 61/500,053, filed Jun. 22, 2011, which is incorporated by reference herein in its entirety. In one embodiment, provided herein are solid forms (e.g., crystal forms, amorphous forms, or mixtures thereof) of isotopologues of Pomalidomide provided herein.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids or bases know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like.

Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts and the calcium, magnesium, sodium or potassium salts in particular. Suitable organic bases include, but are not limited to, N,N-dibenzylethylenediamine, chloroprocaine, choline, diethanolamine, ethylenediamine, meglumaine (N-methylglucamine), lysine, and procaine.

As used herein and unless otherwise indicated, the term "prodrug" means a derivative of a compound that can hydrolyze, oxidize, or otherwise react under biological conditions (in vitro or in vivo) to provide the compound. Examples of prodrugs include, but are not limited to, derivatives of 4-amino-2-(2,6-dioxo-piperidine-3-yl)-isoindoline-1,3-dione that comprise biohydrolyzable moieties such as biohydrolyzable amides, biohydrolyzable esters, biohydrolyzable carbamates, biohydrolyzable carbonates, biohydrolyzable ureides, and biohydrolyzable phosphate analogues. Other examples of prodrugs include derivatives of 4-amino-2-(2,6-dioxo-piperidine-3-yl)-isoindoline-1,3-dione that comprise —NO, —NO$_2$, —ONO, or —ONO$_2$ moieties. Prodrugs can typically be prepared using well-known methods, such as those described in 1 *Burger's Medicinal Chemistry and Drug Discovery*, 172-178, 949-982 (Manfred E. Wolff ed., 5th ed. 1995), and *Design of Prodrugs* (H. Bundgaard ed., Elselvier, New York 1985).

As used herein and unless otherwise indicated, the terms "biohydrolyzable amide," "biohydrolyzable ester," "biohydrolyzable carbamate," "biohydrolyzable carbonate," "biohydrolyzable ureide," "biohydrolyzable phosphate" mean an amide, ester, carbamate, carbonate, ureide, or phosphate, respectively, of a compound that either: 1) does not interfere with the biological activity of the compound but can confer upon that compound advantageous properties in vivo, such as uptake, duration of action, or onset of action; or 2) is biologically inactive but is converted in vivo to the biologically active compound. Examples of biohydrolyzable esters include, but are not limited to, lower alkyl esters, lower acyloxyalkyl esters (such as acetoxylmethyl, acetoxyethyl, aminocarbonyloxymethyl, pivaloyloxymethyl, and pivaloyloxyethyl esters), lactonyl esters (such as phthalidyl and thiophthalidyl esters), lower alkoxyacyloxyalkyl esters (such as methoxycarbonyl-oxymethyl, ethoxycarbonyloxyethyl and isopropoxycarbonyloxyethyl esters), alkoxyalkyl esters, choline esters, and acylamino alkyl esters (such as acetamidomethyl esters). Examples of biohydrolyzable amides include, but are not limited to, lower alkyl amides, α-amino acid amides, alkoxyacyl amides, and alkylaminoalkylcarbonyl amides. Examples of biohydrolyzable carbamates include, but are not limited to, lower alkylamines, substituted ethylenediamines, amino acids, hydroxyalkylamines, heterocyclic and heteroaromatic amines, and polyether amines.

4-amino-2-(2,6-dioxo-piperidine-3-yl)-isoindoline-1,3-dione contains a chiral center, and thus can exist as a racemic mixture of R and S enantiomers. Provided herein is the use of stereomerically pure forms of this compound, as well as the use of mixtures of those forms. For example, mixtures comprising equal or unequal amounts of the enantiomers may be used in methods and compositions. These isomers may be asymmetrically synthesized or resolved using standard techniques such as chiral columns or chiral resolving agents. See, e.g., Jacques, J., et al., *Enantiomers, Racemates and Resolutions* (Wiley-Interscience, New York, 1981); Wilen, S. H., et al., *Tetrahedron* 33:2725 (1977); Eliel, E. L., *Stereochemistry of Carbon Compounds* (McGraw-Hill, N Y, 1962); and Wilen, S. H., *Tables of Resolving Agents and Optical Resolutions* p. 268 (E. L. Eliel, Ed., Univ. of Notre Dame Press, Notre Dame, Ind., 1972).

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound. As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center. In other words, encompassed is the use of the R or S enantiomer of 4-amino-2-(2,6-dioxo-piperidine-3-yl)-isoindoline-1,3-dione in the methods.

It should be noted that if there is a discrepancy between a depicted structure and a name given that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

Citation of any references in this Section is not to be construed as an admission that such references are prior art to the present application.

5.2 Second Active Agents 4-amino-2-(2,6-dioxo-piperidine-3-yl)-isoindoline-1,3-dione can be used with or combined with other pharmacologically active compounds ("second active agents or ingredients") in methods and compositions. It is believed that certain combinations work synergistically in the treatment of particular types of cancer. 4-amino-2-(2,6-dioxo-piperidine-3-yl)-isoindoline-1,3-dione can also work to alleviate adverse effects associated with certain second active agents, and some second active agents can be used to alleviate adverse effects associated with 4-amino-2-(2,6-dioxo-piperidine-3-yl)-isoindoline-1,3-dione.

One or more second active ingredients or agents can be used in the methods and compositions together with 4-amino-2-(2,6-dioxo-piperidine-3-yl)-isoindoline-1,3-dione. Second active agents can be large molecules (e.g., proteins) or small molecules (e.g., synthetic inorganic, organometallic, or organic molecules).

Examples of large molecule active agents include, but are not limited to, hematopoietic growth factors, cytokines, and monoclonal and polyclonal antibodies. Typical large molecule active agents are biological molecules, such as naturally occurring or artificially made proteins. Proteins that are particularly useful include proteins that stimulate the survival and/or proliferation of hematopoietic precursor cells and immunologically active poietic cells in vitro or in vivo. Others stimulate the division and differentiation of committed erythroid progenitors in cells in vitro or in vivo. Particular proteins include, but are not limited to: interleukins, such as IL-2 (including recombinant IL-II ("rIL2") and canarypox IL-2), IL-10, IL-12, and IL-18; interferons, such as interferon alfa-2a, interferon alfa-2b, interferon alfa-n1, interferon alfa-n3, interferon beta-I a, and interferon gamma-I b; GM-CF and GM-CSF; and EPO.

Particular proteins that can be used in the methods and include, but are not limited to: filgrastim, which is sold in the United States under the trade name Neupogen® (Amgen, Thousand Oaks, Calif.); sargramostim, which is sold in the United States under the trade name Leukine® (Immunex, Seattle, Wash.); and recombinant EPO, which is sold in the United States under the trade name Epogen® (Amgen, Thousand Oaks, Calif.).

Recombinant and mutated forms of GM-CSF can be prepared as described in U.S. Pat. Nos. 5,391,485; 5,393,870; and 5,229,496; all of which are incorporated herein by reference. Recombinant and mutated forms of G-CSF can be prepared as described in U.S. Pat. Nos. 4,810,643; 4,999,291; 5,528,823; and 5,580,755; all of which are incorporated herein by reference.

Provided herein are the use of native, naturally occurring, and recombinant proteins. Provided herein are mutants and derivatives (e.g., modified forms) of naturally occurring proteins that exhibit, in vivo, at least some of the pharmacological activity of the proteins upon which they are based. Examples of mutants include, but are not limited to, proteins that have one or more amino acid residues that differ from the corresponding residues in the naturally occurring forms of the proteins. Also encompassed by the term "mutants" are proteins that lack carbohydrate moieties normally present in their naturally occurring forms (e.g., nonglycosylated forms). Examples of derivatives include, but are not limited to, pegylated derivatives and fusion proteins, such as proteins formed by fusing IgG1 or IgG3 to the protein or active portion of the protein of interest. See, e.g., Penichet, M. L. and Morrison, S. L., *J. Immunol. Methods* 248:91-101 (2001).

Antibodies that can be used in combination with compounds provided herein include monoclonal and polyclonal antibodies. Examples of antibodies include, but are not limited to, trastuzumab (Herceptin®), rituximab (Rituxan®), bevacizumab (Avastin™), pertuzumab (Omnitarg™), tositumomab (Bexxar®), edrecolomab (Panorex®), and G250. Compounds provided herein can also be combined with, or used in combination with, anti-TNF-α antibodies.

Large molecule active agents may be administered in the form of anti-cancer vaccines. For example, vaccines that secrete, or cause the secretion of, cytokines such as IL-2, G-CSF, and GM-CSF can be used in the methods, pharmaceutical compositions, and kits. See, e.g., Emens, L. A., et al., *Curr. Opinion Mol. Ther.* 3(1):77-84 (2001).

In one embodiment provided herein, the large molecule active agent reduces, eliminates, or prevents an adverse effect associated with the administration of 4-amino-2-(2,6-dioxo-piperidine-3-yl)-isoindoline-1,3-dione. Depending on the disease or disorder begin treated, adverse effects can include, but are not limited to, drowsiness and somnolence, dizziness and orthostatic hypotension, neutropenia, infections that result from neutropenia, increased HIV-viral load, bradycardia, Stevens-Johnson Syndrome and toxic epidermal necrolysis, and seizures (e.g., grand mal convulsions). A specific adverse effect is neutropenia.

Second active agents that are small molecules can also be used to alleviate adverse effects associated with the administration of 4-amino-2-(2,6-dioxo-piperidine-3-yl)-isoindoline-1,3-dione. However, like some large molecules, many are believed to be capable of providing a synergistic effect when administered with (e.g., before, after or simultaneously) 4-amino-2-(2,6-dioxo-piperidine-3-yl)-isoindoline-1,3-dione. Examples of small molecule second active agents include, but are not limited to, anti-cancer agents, antibiotics, immunosuppressive agents, and steroids.

Examples of anti-cancer agents include, but are not limited to: acivicin; aclarubicin; acodazole hydrochloride; acronine; adozelesin; aldesleukin; altretamine; ambomycin; ametantrone acetate; amsacrine; anastrozole; anthramycin; asparaginase; asperlin; azacitidine; azetepa; azotomycin; batimastat; benzodepa; bicalutamide; bisantrene hydrochloride; bisnafide dimesylate; bizelesin; bleomycin sulfate; bortezomib (Velcade®); brequinar sodium; bropirimine; busulfan; cactinomycin; calusterone; caracemide; carbetimer; carboplatin; carmustine; carubicin hydrochloride; carzelesin; cedefingol; celecoxib (COX-2 inhibitor); chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; iproplatin; irinotecan; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; taxotere; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; and zorubicin hydrochloride.

Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix;

anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; doxorubicin; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imatinib (e.g., Gleevec®); imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mitoguazone; mitolactol; mitomycin analogues; mitonafide; mitotoxin fibroblast growth factor-saporin; mitoxantrone; mofarotene; molgramostim; Erbitux, human chorionic gonadotrophin; monophosphoryl lipid A+myobacterium cell wall sk; mopidamol; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; nilutamide; nisamycin; nitric oxide modulators; nitroxide antioxidant; nitrullyn; oblimersen (Genasense®); $O^6$-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives; palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; perillyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RII retinamide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stipiamide; stromelysin inhibitors; sulfinosine; superactive vasoactive intestinal peptide antagonist; suradista; suramin; swainsonine; tallimustine; tamoxifen methiodide; tauromustine; tazarotene; tecogalan sodium; tegafur; tellurapyrylium; telomerase inhibitors; temoporfin; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; velaresol; veramine; verdins; verteporfin; vinorelbine; vinxaltine; vitaxin; vorozole; zanoterone; zeniplatin; zilascorb; and zinostatin stimalamer.

Specific second active agents include, but are not limited to, rituximab, bortezomib, oblimersen (Genasense®), remicade, docetaxel, celecoxib, melphalan, dexamethasone (Decadro®), steroids, gemcitabine, cisplatinum, temozolomide, etoposide, cyclophosphamide, temodar, carboplatin, procarbazine, gliadel, tamoxifen, topotecan, methotrexate, Arisa®, taxol, taxotere, fluorouracil, leucovorin, irinotecan, xeloda, CPT-11, interferon alpha, pegylated interferon alpha (e.g., PEG INTRON-A), capecitabine, cisplatin, thiotepa, fludarabine, carboplatin, liposomal daunorubicin, cytarabine, doxetaxol, paclitaxel, vinblastine, IL-2, GM-CSF, dacarbazine, vinorelbine, zoledronic acid, palmitronate, biaxin, busulphan, prednisone, bisphosphonate, arsenic trioxide, vincristine, doxorubicin (Doxil®), paclitaxel, ganciclovir, adriamycin, estramustine sodium phosphate (Emcyt®), sulindac, and etoposide.

5.3 Methods of Treatments and Prevention

Methods provided herein encompass those for treating, preventing or managing various types of cancer. In a preferred embodiment, methods encompass those for treating, preventing or managing various types of cancer including but not limited to primary central nervous system lymphoma ("PCNSL"), primary vitreoretinal lymphoma ("PVRL"), intra-ocular lymphoma, central nervous system blastoid mantle cell lymphoma, central nervous system tumors, central nervous system solid tumors, central nervous system cancerous conditions, neuroblastoma, mantle cell lymphoma ("MCL"), lymphocytic lymphoma of intermediate differentiation, intermediate lymphocytic lymphoma ("ILL"), diffuse poorly differentiated lymphocytic lymphoma ("PDL"), centrocytic lymphoma, diffuse small-cleaved cell lymphoma ("DSCCL"), follicular lymphoma, mantle zone lymphoma, and any type of the mantle cell lymphomas that can be seen under the microscope (nodular, diffuse, blastic and mantle zone lymphoma).

In certain embodiments, the cancer is selected from the group consisting of neuroepithelial tumors (e.g., ependymal tumors), tumors of meninges, nerve sheath tumors, glioblastoma, and astrocytoma (e.g., pilocytic astrocytoma). Ependymal tumors and other neuroepithelial tumors are common for children (ages 0-19).

In certain embodiments, the cancer is selected from the group consisting of tumors of meninges, neuroepithelial tumors (e.g., ependymal tumors), nerve sheath tumors, glioblastoma, astrocytoma (e.g., pilocytic astrocytoma), lymphoma, hemangioma, and neoplasam. Tumors of meninges are common for adults (ages 20+).

In certain embodiments, the cancer is located at meninges, pituitary, pineal, nasal cavity, frontal lobe, temporal lobe, parietal lobe, occipital lobe, cerebrum, ventricle, cerebellum, brain stem, spinal cord, cauda equina, cranial nerves, other parts of brain, or other parts of the nervous system.

In certain embodiments, the cancer is selected from the group consisting of meningioma, glioblastoma, tumors of the pituitary, nerve sheath tumors (e.g., acoustic neuromas), neuroepithelial tumors (e.g., ependymal tumors), craniopharyngioma, lymphoma, germ cell tumors, astrocytomas, oligodendrogliomas, and embryonal tumors.

In certain embodiments, the cancer is gliomas. In some embodiments, the gliomas is located at frontal lobe, temporal lobe, parietal lobe, occipital lobe, cerebrum, ventricle, cerebellum, brain stem, spinal cord, cauda equine, cranial nerves, other parts of brain, and other parts of the nervous system. In some embodiments, the gliomas is selected from the group consisting of glioblastoma, astrocytoma (e.g., anaplastic astrocytoma, diffuse astrocytoma, pilocytic astrocytoma), oligoastrocytic tumors, oligodendroglioma, ependymal tumors, and glioma malignant NOS.

In one embodiment, the cancer is refractory, relapsed, or is resistant to chemotherapy other than 4-amino-2-(2,6-dioxo-piperidine-3-yl)-isoindoline-1,3-dione.

As used herein, unless otherwise specified, the term "treating" refers to the administration of a compound, or other additional active agent, after the onset of symptoms of the particular cancer. As used herein, unless otherwise specified, the term "preventing" refers to the administration prior to the onset of symptoms, particularly to patients at risk of cancer. The term "prevention" includes the inhibition of a symptom of the particular cancer. Patients with familial history of cancer in particular are preferred candidates for preventive regimens. As used herein and unless otherwise indicated, the term "managing" encompasses preventing the recurrence of the particular cancer in a patient who had suffered from it, lengthening the time a patient who had suffered from the cancer remains in remission, and/or reducing mortality rates of the patients.

As used herein, the term "cancer" includes, but is not limited to, solid tumors and blood born tumors. The term "cancer" refers to disease of skin tissues, organs, blood, and vessels, including, but not limited to, cancers of the bladder, bone or blood, brain, central nervous system, breast, cervix, chest, colon, endrometrium, esophagus, eye, head, kidney, liver, lymph nodes, lung, mouth, neck, ovaries, pancreas, prostate, rectum, stomach, testis, throat, and uterus. Specific cancers include, but are not limited to, advanced malignancy, amyloidosis, neuroblastoma, meningioma, hemangiopericytoma, multiple brain metastase, glioblastoma multiforms, glioblastoma, brain stem glioma, poor prognosis malignant brain tumor, malignant glioma, recurrent malignant glioma, anaplastic astrocytoma, anaplastic oligodendroglioma, neuroendocrine tumor, rectal adenocarcinoma, Dukes C & D colorectal cancer, unresectable colorectal carcinoma, metastatic hepatocellular carcinoma, Kaposi's sarcoma, karotype acute myeloblastic leukemia, Hodgkin's lymphoma, non-Hodgkin's lymphoma, cutaneous T-Cell lymphoma, cutaneous B-Cell lymphoma, diffuse large B-Cell lymphoma, low grade follicular lymphoma, mantle cell lymphoma ("MCL"), lymphocytic lymphoma of intermediate differentiation, intermediate lymphocytic lymphoma ("ILL"), diffuse poorly differentiated lymphocytic lymphoma ("PDL"), centrocytic lymphoma, diffuse small-cleaved cell lymphoma ("DSCCL"), follicular lymphoma, any type of the mantle cell lymphomas that can be seen under the microscope (nodular, diffuse, blastic and mantle zone lymphoma), malignant melanoma, malignant mesothelioma, malignant pleural effusion mesothelioma syndrome, peritoneal carcinoma, papillary serous carcinoma, gynecologic sarcoma, soft tissue sarcoma, scleroderma, cutaneous vasculitis, Langerhans cell histiocytosis, leiomyosarcoma, fibrodysplasia ossificans progressive, hormone refractory prostate cancer, resected high-risk soft tissue sarcoma, unrescectable hepatocellular carcinoma, Waldenstrom's macroglobulinemia, smoldering myeloma, indolent myeloma, fallopian tube cancer, androgen independent prostate cancer, androgen dependent stage IV non-metastatic prostate cancer, hormone-insensitive prostate cancer, chemotherapy-insensitive prostate cancer, papillary thyroid carcinoma, follicular thyroid carcinoma, medullary thyroid carcinoma, and leiomyoma. In a specific embodiment, the cancer is metastatic. In another embodiment, the cancer is refractory or resistance to chemotherapy or radiation.

The term "lymphoma" refers a heterogenous group of neoplasms arising in the reticuloendothelial and lymphatic systems. Non-Hodgkin's lymphoma ("NHL") refers to malignant monoclonal proliferation of lymphoid cells in sites of the immune system, including lymph nodes, bone marrow, spleen, liver and gastrointestinal tract. The NHL includes, but is not limited to, mantle cell lymphoma ("MCL"), lymphocytic lymphoma of intermediate differentiation, intermediate lymphocytic lymphoma ("ILL"), diffuse poorly differentiated lymphocytic lymphoma ("PDL"), centrocytic lymphoma, diffuse small-cleaved cell lymphoma ("DSCCL"), follicular lymphoma, and any type of the mantle cell lymphomas that can be seen under the microscope (nodular, diffuse, blastic and mantle zone lymphoma). The term lymphoma also encompasses types associated with the central nervous system.

The term "relapsed" refers to a situation where patients who have had a remission of cancer after therapy have a return of a cancerous condition. The term "refractory or resistant" refers to a circumstance where patients, even after intensive treatment, have a residual cancerous condition.

Provided herein are methods of treating patients who have been previously treated for cancer, but are non-responsive to standard therapies, as well as those who have not previously been treated. Also, provided herein are methods of treating patients regardless of patient's age, although some cancers are more common in certain age groups. Further, herein provided are methods of treating patients who have undergone surgery in an attempt to treat the cancer at issue, as well as those who have not. Because patients with cancer have heterogenous clinical manifestations and varying clinical outcomes, the treatment given to a patient may vary, depending on his/her prognosis. The skilled clinician will be able to readily determine without undue experimentation specific secondary agents, types of surgery, and types of non-drug based standard therapy that can be effectively used to treat an individual patient with cancer.

Provided herein are methods comprise administering 4-amino-2-(2,6-dioxo-piperidine-3-yl)-isoindoline-1,3-dione, or a pharmaceutically acceptable salt, solvate (e.g., hydrate), stereoisomer, clathrate, or prodrug thereof, to a patient (e.g., a human) suffering, or likely to suffer, from cancer.

In one embodiment, 4-amino-2-(2,6-dioxo-piperidine-3-yl)-isoindoline-1,3-dione can be administered orally and in single or divided daily doses in an amount of from about 0.10 to about 150 mg/day. In a preferred embodiment, 4-amino-2-(2,6-dioxo-piperidine-3-yl)-isoindoline-1,3-dione may be administered in an amount of from about 0.10 to 150 mg per day, from about 0.5 to about 50 mg per day, or from about 1 to about 10 mg per day. Specific doses per day include 0.1, 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 mg per day.

In a preferred embodiment, 4-amino-2-(2,6-dioxo-piperidine-3-yl)-isoindoline-1,3-dione may be administered in an amount of from about 0.1 to 50 mg per day, or from about 0.5 to about 25 mg per day to patients with various types of cancer including but not limited to primary central nervous system lymphoma ("PCNSL"), primary vitreoretinal lymphoma ("PVRL"), intra-ocular lymphoma, central nervous system blastoid mantle cell lymphoma, central nervous system tumors, central nervous system solid tumors, central nervous system cancerous conditions, mantle cell lymphoma ("MCL"), lymphocytic lymphoma of intermediate differentiation, intermediate lymphocytic lymphoma ("ILL"), diffuse poorly differentiated lymphocytic lymphoma ("PDL"), centrocytic lymphoma, diffuse small-cleaved cell lymphoma ("DSCCL"), follicular lymphoma, mantle zone lymphoma, and any type of the mantle cell lymphomas that can be seen under the microscope (nodular, diffuse, blastic and mantle zone lymphoma).

In particular, 4-amino-2-(2,6-dioxo-piperidine-3-yl)-isoindoline-1,3-dione may be administered to patients with mantle cell lymphoma in an amount of from about 0.1 to 50 mg per day, or from about 0.5 to about 25 mg per day. In a specific embodiment, 4-amino-2-(2,6-dioxo-piperidine-3-yl)-isoindoline-1,3-dione may be administered to patients with cancer in an amount of about 0.5, 1, 2, 3, 4, 5, 10, 15, 20, 25 or 50 mg per day. In a specific embodiment, 4-amino-2-(2,6-dioxo-piperidine-3-yl)-isoindoline-1,3-dione can be administered in an amount of about 4 mg per day to patients with cancer.

In one embodiment, the recommended starting dose of 4-amino-2-(2,6-dioxo-piperidine-3-yl)-isoindoline-1,3-dione is 0.5 mg per day. The dose can be escalated every week to 1, 1.5, 2, 2.5, 3, 3.5, 4, 4.5, 5 and 10 mg per day. The patients who are dosed initially at 4 mg and who experience thrombocytopenia or neutropenia that develops within or after the first four weeks of starting 4-amino-2-(2,6-dioxo-piperidine-3-yl)-isoindoline-1,3-dione therapy may have their dosage adjusted according to a platelet count or absolute neutrophil count ("ANC").

5.3.1 Combination Therapy with a Second Active Agent

Specific methods comprise administering 4-amino-2-(2,6-dioxo-piperidine-3-yl)-isoindoline-1,3-dione, or a pharmaceutically acceptable salt, solvate (e.g., hydrate), stereoisomer, clathrate, or prodrug thereof, in combination with one or more second active agents, and/or in combination with radiation therapy, blood transfusions, or surgery. Examples of 4-amino-2-(2,6-dioxo-piperidine-3-yl)-isoindoline-1,3-dione are disclosed herein (see, e.g., section 5.1). Examples of second active agents are also disclosed herein (see, e.g., section 5.2).

Administration of 4-amino-2-(2,6-dioxo-piperidine-3-yl)-isoindoline-1,3-dione and the second active agents to a patient can occur simultaneously or sequentially by the same or different routes of administration. The suitability of a particular route of administration employed for a particular active agent will depend on the active agent itself (e.g., whether it can be administered orally without decomposing prior to entering the blood stream) and the disease being treated. A preferred route of administration for 4-amino-2-(2,6-dioxo-piperidine-3-yl)-isoindoline-1,3-dione is orally. Preferred routes of administration for the second active agents or ingredients provided herein are known to those of ordinary skill in the art. See, e.g., *Physicians' Desk Reference*, (2006).

In one embodiment, the second active agent is administered intravenously or subcutaneously and once or twice daily in an amount of from about 1 to about 1,000 mg, from about 5 to about 500 mg, from about 10 to about 375 mg, or from about 50 to about 200 mg. The specific amount of the second active agent will depend on the specific agent used, the type of disease being treated or managed, the severity and stage of disease, and the amount(s) of 4-amino-2-(2,6-dioxo-piperidine-3-yl)-isoindoline-1,3-dione and any optional additional active agents concurrently administered to the patient. In a particular embodiment, the second active agent is rituximab, bortezomib, oblimersen (Genasense®), GM-CSF, G-CSF, EPO, taxotere, irinotecan, dacarbazine, transretinoic acid, topotecan, pentoxifylline, ciprofloxacin, dexamethasone, vincristine, doxorubicin, COX-2 inhibitor, IL2, IL8, IL18, IFN, Ara-C, vinorelbine, or a combination thereof.

In a specific embodiment, 4-amino-2-(2,6-dioxo-piperidine-3-yl)-isoindoline-1,3-dione is administered in combination with rituximab to patients with cancer. In a specific embodiment, 4-amino-2-(2,6-dioxo-piperidine-3-yl)-isoindoline-1,3-dione is administered to patients with cancer in an amount of from about 0.1 to about 25 mg per day in combination with rituximab in an amount of 375 mg/m$^2$ by intravenous infusion weekly.

In a preferred embodiment, 4-amino-2-(2,6-dioxo-piperidine-3-yl)-isoindoline-1,3-dione is administered alone or in combination with rituximab to patients with various types of cancer including but not limited to primary central nervous system lymphoma ("PCNSL"), primary vitreoretinal lymphoma ("PVRL"), intra-ocular lymphoma, central nervous system blastoid mantle cell lymphoma, central nervous system tumors, central nervous system solid tumors, central nervous system cancerous conditions, mantle cell lymphoma ("MCL"), lymphocytic lymphoma of intermediate differentiation, intermediate lymphocytic lymphoma ("ILL"), diffuse poorly differentiated lymphocytic lymphoma ("PDL"), centrocytic lymphoma, diffuse small-cleaved cell lymphoma ("DSCCL"), follicular lymphoma, mantle zone lymphoma, and any type of the mantle cell lymphomas that can be seen under the microscope (nodular, diffuse, blastic and mantle zone lymphoma).

In another embodiment, 4-amino-2-(2,6-dioxo-piperidine-3-yl)-isoindoline-1,3-dione is administered alone or in combination with a second active ingredient such as vinblastine or fludarabine to patients with various types of cancer including but not limited to primary central nervous system lymphoma ("PCNSL"), primary vitreoretinal lymphoma ("PVRL"), intra-ocular lymphoma, central nervous system blastoid mantle cell lymphoma, central nervous system tumors, central nervous system solid tumors, central nervous system cancerous conditions, mantle cell lymphoma ("MCL"), lymphocytic lymphoma of intermediate differentiation, intermediate lymphocytic lymphoma ("ILL"), diffuse poorly differentiated lymphocytic lymphoma ("PDL"), centrocytic lymphoma, diffuse small-cleaved cell lymphoma ("DSCCL"), follicular lymphoma, mantle zone lymphoma, and any type of the mantle cell lymphomas that can be seen under the microscope (nodular, diffuse, blastic and mantle zone lymphoma).

In another embodiment, 4-amino-2-(2,6-dioxo-piperidine-3-yl)-isoindoline-1,3-dione is administered in combination with a second active ingredient as follows: temozolomide to pediatric patients with relapsed or progressive brain tumors or recurrent neuroblastoma; celecoxib, etoposide and cyclophosphamide for relapsed or progressive CNS cancer; temodar to patients with recurrent or progressive meningioma, malignant meningioma, hemangiopericytoma, multiple brain metastases, relapsed brain tumors, or newly diagnosed glioblastoma multiforms; irinotecan to patients with recurrent glioblastoma; carboplatin to pediatric patients with brain stem glioma; procarbazine to pediatric patients with progressive malignant gliomas; cyclophosphamide to patients with poor prognosis malignant brain tumors, newly diagnosed or recurrent glioblastoma multiforms; Gliadel® for high grade recurrent malignant gliomas; temozolomide and tamoxifen for anaplastic astrocytoma; or topotecan for gliomas, glioblastoma, anaplastic astrocytoma or anaplastic oligodendroglioma.

In another embodiment, GM-CSF, G-CSF or EPO is administered subcutaneously during about five days in a four or six week cycle in an amount of from about 1 to about 750 mg/m$^2$/day, preferably in an amount of from about 25 to about 500 mg/m$^2$/day, more preferably in an amount of from about 50 to about 250 mg/m$^2$/day, and most preferably in an amount of from about 50 to about 200 mg/m$^2$/day. In a certain embodiment, GM-CSF may be administered in an amount of from about 60 to about 500 mcg/m$^2$ intravenously over 2 hours, or from about 5 to about 12 mcg/m$^2$/day subcutaneously. In a specific embodiment, G-CSF may be administered subcutaneously in an amount of about 1 mcg/kg/day initially and can be adjusted depending on rise of total granulocyte counts. The maintenance dose of G-CSF may be administered in an amount of about 300 (in smaller patients) or 480 mcg subcutaneously. In a certain embodiment, EPO may be administered subcutaneously in an amount of 10,000 Unit 3 times per week.

Also provided herein is a method of increasing the dosage of an anti-cancer drug or agent that can be safely and effectively administered to a patient, which comprises administering to a patient (e.g., a human) 4-amino-2-(2,6-dioxo-piperidine-3-yl)-isoindoline-1,3-dione, or a pharmaceutically acceptable derivative, salt, solvate (e.g., hydrate), or prodrug thereof. Patients that can benefit by this method are those likely to suffer from an adverse effect associated with anti-cancer drugs for treating a specific cancer of the blood, skin, subcutaneous tissue, central nervous system, lymph nodes, brain, lung, liver, bone, intestine, colon, heart, pancreas, adrenal, kidney, prostate, breast, colorectal, or combinations thereof. The administration of 4-amino-2-(2,6-dioxo-piperidine-3-yl)-isoindoline-1,3-dione alleviates or reduces adverse effects which are of such severity that it would otherwise limit the amount of anti-cancer drug.

In one embodiment, 4-amino-2-(2,6-dioxo-piperidine-3-yl)-isoindoline-1,3-dione can be administered orally and daily in an amount of from about 0.10 to about 150 mg, and preferably from about 0.5 to about 50 mg, more preferably from about 1 to about 25 mg prior to, during, or after the occurrence of the adverse effect associated with the administration of an anti-cancer drug to a patient. In a particular embodiment, 4-amino-2-(2,6-dioxo-piperidine-3-yl)-isoindoline-1,3-dione is administered in combination with specific agents such as heparin, aspirin, coumadin, or G-CSF to avoid adverse effects that are associated with anti-cancer drugs such as but not limited to neutropenia or thrombocytopenia.

In another embodiment, provided herein are methods for treating, preventing and/or managing cancer, which comprises administering 4-amino-2-(2,6-dioxo-piperidine-3-yl)-isoindoline-1,3-dione provided herein, or a pharmaceutically acceptable salt, solvate (e.g., hydrate), stereoisomer, clathrate, or prodrug thereof, in conjunction with (e.g., before, during, or after) conventional therapy including, but not limited to, surgery, immunotherapy, biological therapy, radiation therapy, or other non-drug based therapy presently used to treat, prevent or manage cancer. The combined use of the 4-amino-2-(2,6-dioxo-piperidine-3-yl)-isoindoline-1,3-dione provided herein and conventional therapy may provide a unique treatment regimen that is unexpectedly effective in certain patients. Without being limited by theory, it is believed that 4-amino-2-(2,6-dioxo-piperidine-3-yl)-isoindoline-1,3-dione may provide additive or synergistic effects when given concurrently with conventional therapy.

As discussed elsewhere, provided herein are methods of reducing, treating and/or preventing adverse or undesired effects associated with conventional therapy including, but not limited to, surgery, chemotherapy, radiation therapy, hormonal therapy, biological therapy and immunotherapy. 4-amino-2-(2,6-dioxo-piperidine-3-yl)-isoindoline-1,3-dione and other active ingredients can be administered to a patient prior to, during, or after the occurrence of the adverse effect associated with conventional therapy.

In one embodiment, 4-amino-2-(2,6-dioxo-piperidine-3-yl)-isoindoline-1,3-dione can be administered in an amount of from about 0.10 to about 150 mg, and preferably from about 0.5 to about 50 mg, more preferably from about 1 to about 25 mg orally and daily alone, or in combination with a second active agent disclosed herein (see, e.g., section 5.2), prior to, during, or after the use of conventional therapy.

5.3.2 Use with Transplantation Therapy

Compounds provided herein can be used to reduce the risk of Graft Versus Host Disease ("GVHD"). Therefore, provided herein are methods of treating, preventing and/or managing cancer, which comprises administering 4-amino-2-(2,6-dioxo-piperidine-3-yl)-isoindoline-1,3-dione, or a pharmaceutically acceptable salt, solvate (e.g., hydrate), stereoisomer, clathrate, or prodrug thereof, in conjunction with transplantation therapy.

As those of ordinary skill in the art are aware, the treatment of cancer is often based on the stages and mechanism of the disease. For example, as inevitable leukemic transformation develops in certain stages of cancer, transplantation of peripheral blood stem cells, hematopoietic stem cell preparation or bone marrow may be necessary. The combined use of 4-amino-2-(2,6-dioxo-piperidine-3-yl)-isoindoline-1,3-dione and transplantation therapy provides a unique and unexpected synergism. In particular, 4-amino-2-(2,6-dioxo-piperidine-3-yl)-isoindoline-1,3-dione exhibits immunomodulatory activity that may provide additive or synergistic effects when given concurrently with transplantation therapy in patients with cancer.

4-amino-2-(2,6-dioxo-piperidine-3-yl)-isoindoline-1,3-dione can work in combination with transplantation therapy reducing complications associated with the invasive procedure of transplantation and risk of GVHD. Provided herein are methods for treating, preventing and/or managing cancer which comprises administering to a patient (e.g., a human) 4-amino-2-(2,6-dioxo-piperidine-3-yl)-isoindoline-1,3-dione, or a pharmaceutically acceptable salt, solvate (e.g., hydrate), stereoisomer, clathrate, or prodrug thereof, before, during, or after the transplantation of umbilical cord blood, placental blood, peripheral blood stem cell, hematopoietic stem cell preparation or bone marrow. Examples of stem cells suitable for use in the methods provided herein are disclosed in U.S. patent publication nos. 2002/0123141, 2003/0235909 and 2003/0032179, by R. Hariri et al., the entireties of which are incorporated herein by reference.

In one embodiment of this method, 4-amino-2-(2,6-dioxo-piperidine-3-yl)-isoindoline-1,3-dione is administered to patients with lymphomas before, during, or after the transplantation of autologous peripheral blood progenitor cell.

In another embodiment, 4-amino-2-(2,6-dioxo-piperidine-3-yl)-isoindoline-1,3-dione is administered to patients with relapsed lymphoma after the stem cell transplantation.

5.3.3 Cycling Therapy

In certain embodiments, the prophylactic or therapeutic agents provided herein are cyclically administered to a patient. Cycling therapy involves the administration of an active agent for a period of time, followed by a rest for a period of time, and repeating this sequential administration. Cycling therapy can reduce the development of resistance to one or more of the therapies, avoid or reduce the side effects of one of the therapies, and/or improves the efficacy of the treatment.

Consequently, in one specific embodiment, 4-amino-2-(2,6-dioxo-piperidine-3-yl)-isoindoline-1,3-dione is administered daily in a single or divided doses in a four to six week cycle with a rest period of about a week or two weeks. The embodiment further allows the frequency, number, and length of dosing cycles to be increased. Thus, another specific embodiment provided herein encompasses the administration of 4-amino-2-(2,6-dioxo-piperidine-3-yl)-isoindoline-1,3-dione for more cycles than are typical when it is administered alone. In yet another specific embodiment, 4-amino-2-(2,6-dioxo-piperidine-3-yl)-isoindoline-1,3-dione is administered for a greater number of cycles that would typically cause dose-limiting toxicity in a patient to whom a second active ingredient is not also being administered.

In one embodiment, 4-amino-2-(2,6-dioxo-piperidine-3-yl)-isoindoline-1,3-dione is administered daily and continuously for three or four weeks at a dose of from about 0.10 to about 150 mg/d followed by a break of one or two weeks. In a particular embodiment, 4-amino-2-(2,6-dioxo-piperidine-3-yl)-isoindoline-1,3-dione is administered in an amount of from about 1 to about 50 mg/day, preferably in an amount of about 4 mg/day for three to four weeks, followed by one week or two weeks of rest in a four or six week cycle.

In a preferred embodiment, 4-amino-2-(2,6-dioxo-piperidine-3-yl)-isoindoline-1,3-dione is administered to patients with various types of cancer, in an amount of about 0.5 mg, 1 mg, 2 mg, 3 mg or 4 mg per day for 21 days followed by seven days rest in a 28 day cycle. In the most preferred embodiment, 4-amino-2-(2,6-dioxo-piperidine-3-yl)-isoindoline-1,3-dione is administered to patients with refractory or relapsed cancers in an amount of about 4 mg per day for 21 days followed by seven days rest in a 28 day cycle.

In one embodiment, 4-amino-2-(2,6-dioxo-piperidine-3-yl)-isoindoline-1,3-dione and a second active agent or ingredient are administered orally, with administration of 4-amino-2-(2,6-dioxo-piperidine-3-yl)-isoindoline-1,3-dione occurring 30 to 60 minutes prior to a second active ingredient, during a cycle of four to six weeks. In another embodiment, 4-amino-2-(2,6-dioxo-piperidine-3-yl)-isoindoline-1,3-dione is administered orally and a second active ingredient is administered by intravenous infusion.

In a specific embodiment, one cycle comprises the administration of from about 0.1 to about 25 mg/day of 4-amino-2-(2,6-dioxo-piperidine-3-yl)-isoindoline-1,3-dione and from about 50 to about 750 mg/m$^2$/day of a second active ingredient daily for three to four weeks and then one or two weeks of rest.

In one embodiment, rituximab can be administered in an amount of 375 mg/m$^2$ as an additional active agent to patients with various types of cancer. In a preferred embodiment, rituximab can be administered in an amount of 375 mg/m$^2$ as an additional active agent to patients with refractory or relapsed cancer. In a preferred embodiment, one cycle comprises the administration of 4-amino-2-(2,6-dioxo-piperidine-3-yl)-isoindoline-1,3-dione given orally daily for 21 days followed by 7 days of rest and 375 mg/m$^2$ of rituximab by intravenous infusion weekly for four weeks.

Typically, the number of cycles during which the combinatorial treatment is administered to a patient will be from about one to about 24 cycles, more typically from about two to about 16 cycles, and even more typically from about four to about three cycles.

5.4 Pharmaceutical Compositions and Dosage Forms

Pharmaceutical compositions can be used in the preparation of individual, single unit dosage forms. Pharmaceutical compositions and dosage forms provided herein comprise 4-amino-2-(2,6-dioxo-piperidine-3-yl)-isoindoline-1,3-dione, or a pharmaceutically acceptable salt, solvate (e.g., hydrate), stereoisomer, clathrate, or prodrug thereof. Pharmaceutical compositions and dosage forms provided herein can further comprise one or more excipients.

Pharmaceutical compositions and dosage forms provided herein can also comprise one or more additional active ingredients. Consequently, pharmaceutical compositions and dosage forms provided herein comprise the active ingredients disclosed herein (e.g., 4-amino-2-(2,6-dioxo-piperidine-3-yl)-isoindoline-1,3-dione and a second active agent). Examples of optional second, or additional, active ingredients are disclosed herein (see, e.g., section 5.2).

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms provided herein will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms encompassed herein will vary from one another will be readily apparent to those skilled in the art. See, e.g., *Remington's Pharmaceutical Sciences,* 18th ed., Mack Publishing, Easton Pa. (1990).

Typical pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided herein are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions provided herein can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. Preferred lactose-free dosage forms comprise active ingredients, microcrystalline cellulose, pre-gelatinized starch, and magnesium stearate.

Further provided herein are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice,* 2d. Ed., Marcel Dekker, NY, N.Y., 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms provided herein can be prepared using anhydrous or low moisture containing ingredients and low moisture or low humidity conditions. Pharmaceutical compositions and dosage forms that comprise lactose and at least one active ingredient that comprises a primary or secondary amine are preferably anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Provided herein are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. However, typical dosage forms provided herein comprise 4-amino-2-(2,6-dioxo-piperidine-3-yl)-isoindoline-1,3-dione or a pharmaceutically acceptable salt, solvate (e.g., hydrate), stereoisomer, clathrate, or prodrug thereof in an amount of from about 0.10 to about 150 mg. Typical dosage forms comprise 4-amino-2-(2,6-dioxo-piperidine-3-yl)-isoindoline-1,3-dione or a pharmaceutically acceptable salt, solvate (e.g., hydrate), stereoisomer, clathrate, or prodrug thereof in an amount of about 0.1, 1, 1.5, 2, 2.5, 3, 4, 5, 7.5, 10, 12.5, 15, 17.5, 20, 25, 50, 100, 150 or 200 mg. In a specific embodiment, a preferred dosage form comprises 4-amino-2-(2,6-dioxo-piperidine-3-yl)-isoindoline-1,3-dione in an amount of about 0.1, 0.5, 1, 2.5, 3, 4, 5, 7.5, 10, 15, 20, 25 or 50 mg. Typical dosage forms comprise the second active ingredient in an amount of 1 to about 1000 mg, from about 5 to about 500 mg, from about 10 to about 350 mg, or from about 50 to about 200 mg. Of course, the specific amount of the anti-cancer drug will depend on the specific agent used, the type of cancer being treated or managed, and the amount(s) of 4-amino-2-(2,6-dioxo-piperidine-3-yl)-isoindoline-1,3-dione and any optional additional active agents concurrently administered to the patient.

5.4.1 Oral Dosage Forms

Pharmaceutical compositions provided herein that are suitable for oral administration can be presented as discrete dosage forms, such as, but are not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 18th ed., Mack Publishing, Easton Pa. (1990).

In one embodiment, a preferred dosage form is a capsule or tablet comprising 4-amino-2-(2,6-dioxo-piperidine-3-yl)-isoindoline-1,3-dione in an amount of about 0.5, 1, 2, 3, 4, 5, 10, 15, 20, 25 or 50 mg. In a specific embodiment, a preferred capsule or tablet dosage form comprises 4-amino-2-(2,6-dioxo-piperidine-3-yl)-isoindoline-1,3-dione in an amount of about 1, 2, 3 or 4 mg.

Typical oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

Because of their ease of administration, tablets and capsules represent the most advantageous oral dosage unit forms, in which case solid excipients are employed. If desired, tablets can be coated by standard aqueous or non-aqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, Pa.), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms disclosed herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions provided herein is typically present in from about 50 to about 99 weight percent of the pharmaceutical composition or dosage form.

Disintegrants are used in the compositions provided herein to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients should be used to form solid oral dosage forms provided herein. The amount of disintegrant used varies based upon the type of formulation, and is readily discernible to those of ordinary skill in the art. Typical pharmaceutical compositions comprise from about 0.5 to about 15 weight percent of disintegrant, preferably from about 1 to about 5 weight percent of disintegrant.

Disintegrants that can be used in pharmaceutical compositions and dosage forms provided herein include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms provided herein include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, Md.), a coagulated aerosol of synthetic silica (marketed by Degussa Co. of Plano, Tex.), CAB-O-SIL (a pyrogenic silicon dioxide product sold by Cabot Co. of Boston, Mass.), and mixtures thereof. If used at all, lubricants are typically used in an amount of less than about 1 weight percent of the pharmaceutical compositions or dosage forms into which they are incorporated.

A preferred solid oral dosage form provided herein comprises 4-amino-2-(2,6-dioxo-piperidine-3-yl)-isoindoline-1,3-dione, anhydrous lactose, microcrystalline cellulose, polyvinylpyrrolidone, stearic acid, colloidal anhydrous silica, and gelatin.

5.4.2 Delayed Release Dosage Forms

Active ingredients provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide slow or controlled-release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled-release formulations known to those of ordinary skill in the art, including those described herein, can be readily selected for use with the active ingredients provided herein. Thus provided herein are single unit dosage forms suitable for oral administration such as, but not limited to, tablets, capsules, gelcaps, and caplets that are adapted for controlled-release.

All controlled-release pharmaceutical products have a common goal of improving drug therapy over that achieved by their non-controlled counterparts. Ideally, the use of an optimally designed controlled-release preparation in medical treatment is characterized by a minimum of drug substance being employed to cure or control the condition in a minimum amount of time. Advantages of controlled-release formulations include extended activity of the drug, reduced dosage frequency, and increased patient compliance. In addition, controlled-release formulations can be used to affect the time of onset of action or other characteristics, such as blood levels of the drug, and can thus affect the occurrence of side (e.g., adverse) effects.

Most controlled-release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled-release of an active ingredient can be stimulated by various conditions including, but not limited to, pH, temperature, enzymes, water, or other physiological conditions or compounds.

5.4.3 Parenteral Dosage Forms

Parenteral dosage forms can be administered to patients by various routes including, but not limited to, subcutaneous, intravenous (including bolus injection), intramuscular, and intraarterial. Because their administration typically bypasses patients' natural defenses against contaminants, parenteral dosage forms are preferably sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms provided herein are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms provided herein. For example, cyclodextrin and its derivatives can be used to increase the solubility of 4-amino-2-(2,6-dioxo-piperidine-3-yl)-isoindoline-1,3-dione and its derivatives. See, e.g., U.S. Pat. No. 5,134,127, which is incorporated herein by reference.

6. EXAMPLES

Certain embodiments provided herein are illustrated by the following non-limiting example.

6.1 Treatment of Central Nervous System Lymphoma
6.1.1 Introduction

Primary central nervous system lymphoma ("PCNSL") is most frequently a diffuse large B cell lymphoma ("DLBCL") confined to the central nervous system ("CNS") and carries a poor prognosis. Ferreri A. J., *Blood,* 2011, 118, pp. 510-522. CNS tumor microenvironment plays an important role in the biology of CNS lymphoma. The standard therapy consists of high-dose methotrexate and high-dose ara-c with or without radiation. Although there has been an improvement in the survival due to these treatments, the prognosis of CNS lymphoma remains poor compared to systemic DLBCL. Id. Current therapeutic agents target lymphoma cells and have no significant impact on the tumor microenvironment. Blood brain barrier is a major obstacle for effective treatment of CNS lymphoma. As such, therapeutic agents with better efficacy, excellent CNS penetration, and impact on the tumor microenvironment as well as lymphoma cells need to be developed.

4-amino-2-(2,6-dioxo-piperidine-3-yl)-isoindoline-1,3-dione (Pomalidomide), a thalidomide analogue and a novel immunomodulatory agent, has shown in vitro activity against lymphoma cell lines and in vivo pre-clinical activity against systemic lymphoma in a murine model. Hernandez-Ilizaliturri, F. J.; et al., *Cancer,* 2011, 117, pp. 5058-5066. Lenalidomide, another thalidomide analogue with immunomodulatory activity, has shown therapeutic activity against activated B cell subtype of systemic diffuse large B cell lymphoma, which is the subtype of DLBCL seen in more than 95% of PCNSL. Hernandez-Ilizaliturri, 2011; Camilleri-Broet, S.; et al., *Blood,* 2006, 107, pp. 190-196. Case reports have also indicated activity of lenalidomide in refractory intra-ocular lymphoma, and blastoid mantle cell lymphoma affecting the CNS. Rubenstein, J. L.; et al., *J. Clin. Oncol.,* 2011, 29, pp. e595-597; Cox, M. C.; et al., *Am. J. Hematol.,* 2011, 86, p. 957.

A comprehensive preclinical study was conducted to determine the therapeutic use of 4-amino-2-(2,6-dioxo-piperidine-3-yl)-isoindoline-1,3-dione against central nervous system lymphoma. Central nervous system ("CNS") pharmacokinetic analysis was performed in rats to assess the CNS penetration of 4-amino-2-(2,6-dioxo-piperidine-3-yl)-isoindoline-1,3-dione. Preclinical evaluation of 4-amino-2-(2,6-dioxo-piperidine-3-yl)-isoindoline-1,3-dione was performed in two murine models to assess its therapeutic activity against CNS lymphoma. The impact of 4-amino-2-(2,6-dioxo-piperidine-3-yl)-isoindoline-1,3-dione on the CNS lymphoma immune microenvironment was evaluated by immunohistochemistry and immunofluorescence. In vitro cell culture experiments were carried out to further investigate the impact of 4-amino-2-(2,6-dioxo-piperidine-3-yl)-isoindoline-1,3-dione on the biology of macrophages.

The compound 4-amino-2-(2,6-dioxo-piperidine-3-yl)-isoindoline-1,3-dione crossed the blood brain barrier with CNS penetration of approximately 39%. Preclinical evaluations showed: (1) it had significant therapeutic activity against CNS lymphoma with significant reduction in tumor growth rate and prolongation of survival; (2) that it had a major impact on the tumor microenvironment with an increase in macrophages and natural killer cells and; (3) and that it decreased M2-polarized tumor-associated macrophages and increased M1-polarized macrophages when macrophages were evaluated based on polarization status. In vitro studies using various macrophage models showed: (1) 4-amino-2-(2,6-dioxo-piperidine-3-yl)-isoindoline-1,3-dione converted the polarization status of IL4-stimulated macrophages from M2 to M1; (2) M2 to M1 conversion by 4-amino-2-(2,6-dioxo-piperidine-3-yl)-isoindoline-1,3-dione in the polarization status of macrophages co-cultured with B lymphoma cells is dependent on the presence of NK cells; (3) 4-amino-2-(2,6-dioxo-piperidine-3-yl)-isoindoline-1,3-dione induced M2 to M1 conversion in the polarization of macrophages by inactivating STAT6 signaling and activating STAT1 signaling and; (4) that functionally, it increased phagocytic activity of macrophages.

The study result shows that 4-amino-2-(2,6-dioxo-piperidine-3-yl)-isoindoline-1,3-dione has excellent CNS penetration, significant preclinical therapeutic activity, a major impact on the tumor microenvironment and is a promising therapeutic agent for CNS lymphoma. Furthermore, 4-amino-2-(2,6-dioxo-piperidine-3-yl)-isoindoline-1,3-dione can induce significant biological changes in tumor-associated macrophages, which likely pay a major role in the therapeutic activity against CNS lymphoma.

6.1.2 Materials and Methods

CNS pharmacokinetic analysis of 4-amino-2-(2,6-dioxo-piperidine-3-yl)-isoindoline-1,3-dione was performed in a Celgene laboratory. The Tun laboratory at Mayo Clinic Florida performed all the other experiments.

CNS Pharmacokinetic Analysis of 4-amino-2-(2,6-dioxo-piperidine-3-yl)-isoindoline-1,3-dione Compounds 4-amino-2-(2,6-dioxo-piperidine-3-yl)-isoindoline-1,3-dione (pomalidomide, MW 273.25, $C_{13}H_{11}N_3O_4$) and CC-6032 (MW 287.27, $C_{14}H_{13}N_3O_4$) from Celgene were used in pharmacokinetic analyses. CC-6032 was used as the probe calibrator in the microdialysis experiment.

Microdialysis: A total of 3 male CD-IGS rats were used. Stomach-cannulated CD-IGS rats (male, weight range: 250-300 g) supplied by Charles River Laboratories were used in this study. Following surgery, all animals were housed in BASi Raturn® containment systems with standard bedding material. Rat chow and water were available ad libitum, and all animals were kept in an ambient temperature room under a 6 am to 6 pm 12-hour lighting schedule.

Animal surgeries consisted of implanting a CMA/20 14/10PC vascular microdialysis probe (Part #8309571, CMA Microdialysis, North Chelmsford, Mass.) in the jugular vein, according to an IACUC protocol. Each animal was then stereotaxically implanted with an intracerebral guide directed toward the top of the striatum (A/P: 0.7, L/M: −3.0, DN: −3.0; from bregma), according to a rat stereotaxic atlas. Paxinos G. F. K., The mouse brain in stereotaxic coordinates (Academic Press, San Diego, Calif.) (2001). A BASi BR-4 brain microdialysis probe (Part # MD-2204, BASi, West Lafayette, Ind.) was inserted prior to recovery, and the probes were slowly perfused (0.5 µL/min) with either sterile lactated Ringer's (brain) or Dulbecco's phosphate-buffered saline (D-PBS; blood). Animals were allowed to recover for at least 24 hours prior to dosing. On the day of dosing, the blank perfusate was replaced with perfusate containing the probe calibrator, and flow was set to 1.25 µl/min. 4-amino-2-(2,6-dioxo-piperidine-3-yl)-isoindoline-1,3-dione was administered as a single p.o. administration via the stomach cannula, at 50 mg/kg (5 mL/kg) in a 0.5% A carboxymethylcellulose/0.25% Tween® 80 suspension formulation.

Microdialysate was collected in a cooling fraction collector, set at 4° C. (Eicom # EFC-82, EFR-82, Eicom, San Diego, Calif.) at intervals of 25 minutes for 10 hours after dosing. To calculate area-under-the-curve (AUC), the corrected concentration of each sample was multiplied by the interval over which the sample was collected; in this case 25 minutes, and divided by 60 minutes per hour. The sum of these values represented the total AUC value over the specified time range. To generate graphs, the concentration at each time point was plotted at the mid-point of each collection interval. Microdialysates were collected at the specified time points and analyzed for 4-amino-2-(2,6-dioxo-piperidine-3-yl)-isoindoline-1,3-dione concentration using a liquid chromatography-tandem mass spectrometry (LC-MS/MS) assay, within 12 hours. Interim storage was at 4° C.

Mass Spectral Analysis: Microdialysate samples were injected directly into the LC-MS/MS system without processing. Chromatographic separation was achieved using a Phenomenex Synergi $C_{18}$ column (50×4.6 mm, 4 µm) with gradient elution of 0.1% formic acid in water and 0.1% formic acid in acetonitrile. Detection and quantitation were performed using positive electrospray in multiple reaction-monitoring ("MRM") modes on a Waters Micromass Ultima tandem mass spectrometer. Transition ions monitored were m/z 274.1 to m/z 84.3 for the analyte and m/z 288.0 to m/z 98.0 for the probe calibrator CC-6032. Calibration was performed using weighted ($1/x^2$) quadratic regression of peak area. Two calibration curves for 4-amino-2-(2,6-dioxo-piperidine-3-yl)-isoindoline-1,3-dione in PBS and lactated ringers solution were constructed using standards at concentrations of 1.28, 2.56, 5.12, 10.2, 25.6, 64.0, 160, 400, 1000, and 2000 ng/mL. A quadratic regression model with a weighting of $1/(x^2)$ was used for the regression of calibration curves. Concentrations below the limit of quantitation ("BLOQ") were treated as zero for calculations.

Preclinical Evaluation of 4-amino-2-(2,6-dioxo-piperidine-3-yl)-isoindoline-1,3-dione Compound 4-amino-2-(2,6-dioxo-piperidine-3-yl)-isoindoline-1,3-dione (Pomalidomide, MW 273.25, $C_{13}H_{11}N_3O_4$) obtained from Celgene Corporation.

Animal and housing: Female athymic mice (8-10 weeks old and weighing 20-25 g at the beginning of the study) were purchased from Harlan laboratories. They were housed in a temperature-controlled sterilized room (23±2° C.) with a 12-h light/dark cycle and free access to food and water throughout the study. Animal use was approved by Mayo Foundation Institutional Animal Use and Care Committee and was in accordance with NIH Guide for the Care and Use of Laboratory Animals.

Orthotopic murine CNS lymphoma models: Two murine CNS lymphoma models were created by intracerebral injection of $2.5 \times 10^4$ luciferase-transfected Raji or $1 \times 10^5$ luciferase-transfected OCI-LY10 B lymphoma cells in athymic mice under anesthesia using a stereotactic platform. Eight-week-old athymic mice underwent minimum 7-day acclimation/quarantine prior to surgery. Surgery was performed in a laminar flow hood under sterile conditions. Tylenol 300 mg/kg PO was given for analgesia 24 hours before the surgery continuing 48 hours postoperatively. Anesthesia was achieved by inhalation of 1-2% isoflurane. After the mouse became well anesthetized, it was placed in the Kopf stereotactic instrument. A small amount of BNP antibiotic cream (a mixture of Bacitracin, Neomycin and Polymyxin) was smeared on its eyes to prevent infection and corneal damage during surgery. A strip of soft fabric was placed over the mouse's body and tail to prevent excessive heat loss during surgery. The scalp area was cleaned with a 2% solution of Betadine and dried with cotton tipped applicator. A midline sagittal incision was made in the scalp. A small burr hole was drilled in the left skull with a surgical drill (Kopf) or a Dremel drill according to the coordinates (AP: 0.5 mm, LM: 2.5 mm) as determined by reference to the mouse brain atlas by Franklin and Paxinos. Paxinos, 2001. The dura mater was surgically exposed, and a 10

μl-Hamilton syringe with a 26S-gauge beveled needle was lowered into the left cerebral hemisphere up to the depth of 3 mm and 5 μl of tumor cells was slowly infused (0.5 μl/min). The needle was left in place for 5 minutes to prevent reflux and then was slowly removed. The skin was closed with wound clips. The mice recovered from anesthesia and surgery in a warm environment and were not returned to their cages until motor activity returned. Cages were placed on top of a heating pad to minimize the loss of body heat during the recovery. The mice were monitored postoperatively at least twice a day for 5 days or until recovery was complete.

Bioluminescence imaging of mouse: After intracerebral injection of lymphoma cells, all the mice were subjected to bioluminesence imaging ("BLI") twice a week starting at day-4 post-intracerebral injection to monitor the real-time in vivo tumor growth. BLI was conducted using a Xenogen Lumina optical imaging system (Caliper Life Sciences, Hopkinton, Mass.). Mice were anesthetized with isofluorane before intraperitoneal injections of luciferin at a dose of 150 mg/kg, providing a saturating substrate concentration for luciferase enzyme. Peak luminescent signals were recorded 10 minutes after luciferin injection. Regions of interest encompassing the intracranial area of signal were defined using Living Image software (Xenogen), and the total photons/s/steradian/$cm^2$ was recorded.

In vivo preclinical evaluation of 4-amino-2-(2,6-dioxo-piperidine-3-yl)-isoindoline-1,3-dione in murine CNS lymphoma models: Mice were imaged 4 days after intracerebral injection and were distributed among different treatment groups with equivalent average BLI signal. Real time tumor growth was monitored by BLI. Tumor growth and survival data were analyzed for statistical difference between the groups. Mice were assigned to four experimental groups and one vehicle control group in Raji model. Mice in experimental groups received 4-amino-2-(2,6-dioxo-piperidine-3-yl)-isoindoline-1,3-dione 0.3 mg/kg, 3 mg/kg, 10 mg/kg, or 30 mg/kg by oral gavage daily for 28 days. Control group received similar volume of vehicle oral daily for 28 days. In the OCI-LY10 model, 4-amino-2-(2,6-dioxo-piperidine-3-yl)-isoindoline-1,3-dione 0.3 mg/kg dose level was not included.

Immunohistochemistry ("IHC") assessment for macrophages: Paraffin sections (10 μm thick) were fixed, blocked, and immunostained with the appropriate antibody: Iba-1 (BD Biosciences) for macrophages, Ym1 (Stemcell Technologies) as a marker for M2 polarization, iNOS (Calbiochem) as a marker for M1 polarization. Aperio ScanScope XT slide scanner and image analysis system (Aperio Spectrum, Vista, Calif.) were used for quantitative assessment of macrophages. Three equal-size (0.4 mM2) fields in macrophage-dense areas were selected in the contralateral brain and the tumor for counting. Data were shown as an average of the three fields.

Immunofluorescence for natural killer cells: Frozen sections (10 μm thick) were permeabilized with PBS-0.2% Triton X-100 for 5 min. After blocking with PBS-5% goat serum-0.02% Triton X-100 for 45 mins at 37° C., the sections were incubated overnight at 4° C. with Rat monoclonal CD335 antibody (a marker for NK cells, 1:200, Biolegend). After washing, sections were incubated with the Alexa Fluor 594 Goat anti-Rat IgG secondary antibody (1:1000, Life Technologies) at 37° C. for 1.5 h. Finally, Vectashield H-1200 mounting medium with DAPI (Vector Laboratories) was used to stain the nuclei. Images were obtained on a Zeiss LSM 510 META confocal microscope. Six equal-size (0.2 $mM^2$) fields in NK-dense areas were selected in the tumor for taking pictures. Fluorescence intensity data were generated by Zeiss LSM 510 and shown as an average of six fields.

Statistical analysis: One-way ANOVA was used to compare the difference between the groups at each time point. Two-way repeated measures ANOVA was used to analyze the interaction between the time and treatment. Survival analysis was performed by Kaplan Meier method. Kaplan Meier survival curves were generated using Prism4 software and the statistical difference between curves was derived with a log-rank test. P<0.05 was considered significant.

In Vitro Cell Culture Experiments to Investigate the Impact of 4-amino-2-(2,6-dioxo-piperidine-3-yl)-isoindoline-1,3-dione on the Biology of Macrophages: Cell Culture and Treatment Raji lymphoma cells (ATCC), U937 human monocyte cells (ATCC) and YTS NK cells (a gift from Dr. Pamela A. Becker) were cultured at 37° C. in a humidified incubator under 5% CO2 and 95% air in RPMI-1640 supplemented with 20% FCS and 1% penicillin-streptomycin, and 1% nonessential amino acids.

OCI-LY10 lymphoma cells (a gift from Arthur L. Shaffer III) were cultured at 37° C. in a humidified incubator under 5% CO2 and 95% air in IMDM supplemented with 20% FCS and 1% penicillin-streptomycin. Co-culture of lymphoma cells and U937 monocytes: Raji and U937 monocytes were cultured at 37° C. in a humidified incubator under 5% CO2 and 95% air in RPMI-1640 supplemented with 20% FCS and 1% penicillin-streptomycin, and 1% nonessential amino acids. OCI-LY10 and U937 monocytes were cultured at 37° C. in a humidified incubator under 5% CO2 and 95% air in IMDM supplemented with 20% FCS and 1% penicillin-streptomycin. Triple culture of lymphoma cells, U937 monocytes and YTS cells: Raji, U937 and YTS cells were cultured at 37° C. in a humidified incubator under 5% CO2 and 95% air in RPMI-1640 supplemented with 20% FCS and 1% penicillin-streptomycin, and 1% nonessential amino acids. OCI-LY10, U937 and YTS were cultured at 37° C. in a humidified incubator under 5% CO2 and 95% air in IMDM supplemented with 20% FCS and 1% penicillin-streptomycin.

Treatments: In experiments in which IL-4 was used to induce M2 polarization of macrophages, cells were treated with IL-4 (20 ng/ml) for 48 hours followed by treatment with 4-amino-2-(2,6-dioxo-piperidine-3-yl)-isoindoline-1, 3-dione (10 ug/ml) or DMSO control for 48 hours. In triple cell culture experiments with lymphoma cells, macrophages, and NK cells, the treatment was with either DMSO or 4-amino-2-(2,6-dioxo-piperidine-3-yl)-isoindoline-1,3-dione (10 ug/ml) for 48 hours.

Immunofluorescence for analysis of macrophage polarization in cell culture experiments: Live cells were fixed in 10% formalin for 30 minutes at room temperature followed by permeabilization with PBS-0.2% Triton X-100 for 2 min. After blocking with PBS-5% goat serum-0.02% Triton X-100 for 30 minutes at 37° C., the cells were incubated overnight at 4° C. with rat monoclonal F4/80 antibody (for primary microglia cells, 1:200 Abcam), rat monoclonal CD11b (for U937, 1:200 Biolegend), rabbit polyclonal Ym1 antibody (for primary microglia cells and primary peritoneal macrophages, 1:200, Stemcell Technologies, Vancouver, Canada), rabbit polyclonal FXIII A antibody (for U937, 1:200, Abcam), mouse monoclonal p-STAT1 antibody (1:200, Abcam), rabbit polyclonal p-STAT6 antibody (1:200, Abcam) or rabbit iNOS antibody (1:200, Calbiochem). After washing, cells were incubated with the Alexa Fluor 594 Goat anti-Rat IgG secondary antibody (1:1000, Life Technologies) and FITC Donkey anti-rabbit IgG secondary antibody (1:1000, Life technology) or FITC Goat anti-mouse IgG secondary antibody (1:1000, Sigma) at 37° C. for 45 minutes. Finally, Vectashield H-1200 mounting medium with DAPI (Vector Laboratories) was used to stain the nuclei. Images were obtained on a Zeiss LSM 510 META confocal microscope.

Phagocytosis assay: The impact of 4-amino-2-(2,6-dioxo-piperidine-3-yl)-isoindoline-1,3-dione on the phagocytic activity of macrophages was assessed in primary microglial cells and human monocyte cells (U937). The cells were cultured in complete medium for 4 days. They were then harvested and resuspended in Opti-MEM medium at 106 cells/ml and seeded in a 96 well plate at 100,000 viable cells/well. The experimental wells were treated with 4-amino-2-(2,6-dioxo-piperidine-3-yl)-isoindoline-1,3-dione 3 or 10 ug/ml. After 48 hours of treatment, the culture medium was quickly replaced with 100 ul of pHrodo BioParticles suspension (Life technologies and the cells were incubated in the suspension at 37° C. for 2-3 hours. Following incubation, the plates were scanned at 550 nm/600 nm (excitation/emission) using fluorescence plate reader. The fluorescence activity reflects the phagocytic activity of the macrophages. The impact of 4-amino-2-(2,6-dioxo-piperidine-3-yl)-isoindoline-1,3-dione treatment (% effect) was calculated as a fraction of the phagocytic activity in the positive control wells. Wan, C. P.; et al., *J. Immunol. Methods*, 1993, 162, pp. 1-7.

6.1.3 Results 4-amino-2-(2,6-dioxo-piperidine-3-yl)-isoindoline-1,3-dione has excellent CNS penetration: 4-amino-2-(2,6-dioxo-piperidine-3-yl)-isoindoline-1,3-dione was shown by a previous study to have desirable pharmacokinetic properties in the rat. Zhu, D.; et al., *Cancer Immunol. Immunother.*, 2008, 1849-1859. It had relatively slow clearance (12.3 mL/min/kg), a reasonable volume of distribution (1.75 L/kg), and an acceptable bioavailability (47.4%). Table 1 and FIG. 1 summarize the brain microdialysis data. Following a 50 mg/kg p.o. administration of pomalidomide to rats, unbound concentrations in blood reached a $C_{max}$ value of 1100±82 ng/mL at 4.6±2.4 hours, with a concomitant $AUC_{(0-10)}$ value of 6800±2000 ng·hr/mL. Unbound 4-amino-2-(2,6-dioxo-piperidine-3-yl)-isoindoline-1,3-dione in the brain, however, had a $C_{max}$ value of 430±63 ng/mL at 4.1±1.5 hours and an $AUC_{(0-10)}$ value of 2700±740 ng·hr/mL, giving an unbound $AUC_{brain}$ to $AUC_{blood}$ ratio of 0.39±0.03. These values are consistent with excellent blood-brain-barrier penetration. The results obtained in this study were consistent with those seen in a concurrent study looking at whole brain 4-amino-2-(2,6-dioxo-piperidine-3-yl)-isoindoline-1,3-dione content following its oral administration to mice.

TABLE 1

Pharmacokinetic parameters of pomalidomide in fasted male CD-IGS rats following a single IV and PO administration at 5 mg/kg and 50 mg/kg, respectively. Mean unbound blood and brain microdialysis parameters for pomalidomide in male CD-IGS rats following a single p.o. administration at 50 mg/kg.

| IV PK Parameters | Mean ± SD CC-4047, n = 5, 5 mg/kg[a] | PO PK Parameters | Mean ± SD CC-4047, n = 4, 50 mg/kg[b] |
|---|---|---|---|
| CL (mL/min/kg) | 12.3 ± 2.6 | $C_{max}$ (ng/mL) | 3372 ± 758 |
| $V_{ss}$ (L/kg) | 1.75 ± 0.2 | $T_{max}$ (hr) | 2.0 ± 0.0 |
| $T_{1/2}$ (hr) | 2.44 ± 0.8 | $AUC_{(0-24)}$ (ng · hr/mL) | 33155 ± 8561 |
| $AUC_{(0-inf)}$ (ng · hr/mL) | 7016 ± 1551 | F (%) | 47.4 ± 15.2 |

| Microdialysis PO PK Parameters (50 mg/kg [c], n = 3) | Mean ± SD | |
|---|---|---|
| | Brain | Blood |
| $C_{max}$ (ng/mL) | 430.0 ± 63 | 1100 ± 82 |
| $T_{max}$ (hr) | 4.10 ± 1.5 | 4.6 ± 2.4 |
| $AUC_{(0-10)}$ (ng · hr/mL) | 2700 ± 740 | 6800 ± 2000 |
| AUC ratio Brain:Blood) | 0.39 ± 0.03 | |

[a]Solution in dimethylacetamide/PEG400/saline (10/50/40)
[b]Suspention in 0.5% CMC/0.25% Tween80 in water
[c]Suspention in 0.5% CMC/0.25% Tween80 in water Single agent oral 4-amino-2-(2,6-dioxo-piperidine-3-yl)-isoindoline-1,3-dione has significant pre-clinical therapeutic activity against CNS lymphoma in murine models: 4-amino-2-(2,6-dioxo-piperidine-3-yl)-isoindoline-1,3-dione showed significant preclinical therapeutic activity against CNS lymphoma in both Raji and OCI-LY10 murine orthotopic models. The findings showed a dose-dependent therapeutic activity against CNS lymphoma with statistically significant therapeutic activity was at 3 mg, 10 mg, and 30 mg/kg dose levels of 4-amino-2-(2,6-dioxo-piperidine-3-yl)-isoindoline-1,3-dione in terms of reduction of tumor growth and prolongation of survival (see FIG. 2). There was a good correlation between control of tumor growth and survival prolongation. The median survival in Raji model was 31 days (30 mg/kg), 27 days (10 mg/kg), 28 days (3 mg/kg), and 24 days (0.3 mg/kg) compared to 21 days with vehicle control group (see FIG. 2A). The median survival in OCI-LY10 model was 40 days (30 mg/kg), 37 days (10 mg/kg), 32 days (3 mg/kg), and compared to 26 days with vehicle control group (see FIG. 2B). Body weight chart showed that mice in 3 mg, 10 mg, and 30 mg/kg treatment groups were able to maintain their body weight better than those in control group.

Also tested was a combination of 4-amino-2-(2,6-dioxo-piperidine-3-yl)-isoindoline-1,3-dione and weekly dexamethasone in the Raji model, showing that addition of dexamethasone led to further improvement in survival. Addition of oral dexamethasone 20 mg/kg weekly for 4 weeks to 4-amino-2-(2,6-dioxo-piperidine-3-yl)-isoindoline-1,3-dione leads to improved outcomes at 10 mg and 30 mg/kg 4-amino-2-(2,6-dioxo-piperidine-3-yl)-isoindoline-1,3-dione dose levels. The median survival was prolonged by 3 days and 5 days respectively by addition of weekly dexamethasone to 4-amino-2-(2,6-dioxo-piperidine-3-yl)-isoindoline-1,3-dione at 10 mg and 30 mg/kg dose levels. (see FIG. 10).

4-amino-2-(2,6-dioxo-piperidine-3-yl)-isoindoline-1,3-dione has a significant impact on the tumor microenvironment in CNS lymphoma: CNS microenvironment plays an important role in CNS lymphoma. Jiang, L.; et al., *Int. J. Clin. Exp. Pathol.*, 2010, 3, pp. 763-767; Tun, H. W.; et al., *Blood*, 2008, 111, pp. 3200-3210. The immunohistochemistry studies on harvested murine brains from the preclinical evaluation showed that 4-amino-2-(2,6-dioxo-piperidine-3- yl)-isoindoline-1,3-dione treatment significantly increased the number of macrophages by Iba-1 stain (see FIGS. 3A & 4A). When macrophages were further studied using Ym1 as a marker of M2 polarization and iNOS as a marker of M1 polarization, 4-amino-2-(2,6-dioxo-piperidine-3-yl)-isoindoline-1,3-dione treatment was found to be associated with a significant decrease in M2-polarized tumor associated macrophages and a significant increase in the number of M1-polarized macrophages (see FIGS. 3B, 4B, & 11). These findings suggested that 4-amino-2-(2,6-dioxo-piperidine-3-yl)-isoindoline-1,3-dione treatment has a significant impact on the polarization status of macrophages. Furthermore, 4-amino-2-(2,6-dioxo-piperidine-3-yl)-isoindoline-1,3-dione treatment also led to a significant increase in the number of NK cells by CD335 stain (see FIG. 5). The increase in the number of macrophages and NK cells was more pronounced in the tumor compared to the cerebral hemisphere contralateral to the implantation site.

4-amino-2-(2,6-dioxo-piperidine-3-yl)-isoindoline-1,3-dione has a major impact on the biology of macrophages: As a significant immunomodulatory impact was seen on macrophages in CNS lymphoma microenvironment by 4-amino-2-(2,6-dioxo-piperidine-3-yl)-isoindoline-1,3-dione treatment in the in vivo preclinical evaluation, we proceeded with in vitro experiments to further elucidate its impact on the biology of macrophages with an emphasis on their polarization status.

The impact of 4-amino-2-(2,6-dioxo-piperidine-3-yl)-isoindoline-1,3-dione on the polarization status of macrophages was studied in various cell models including primary murine microglial cells, primary murine peritoneal macrophages, and human monocyte cell line (U937). As CNS lymphoma microenvironment is rich in IL-4 and as IL-4 is known to induce M2 polarization of macrophages, IL-4 treatment with or without 4-amino-2-(2,6-dioxo-piperidine-3-yl)-isoindoline-1,3-dione treatment was tested on U937 (see FIG. 6), primary microglial cells (see FIG. 11), and primary peritoneal macrophages (see FIG. 12). Kadoch, C.; et al., *Clin. Cancer Res.*, 2009, 15, pp. 1989-1997; Rubenstein, J. L.; et al., *Blood*, 2006, 107, pp. 3716-3723; Mantovani, A.; et al., *Trends Immunol.*, 2002, 23, pp. 549-555. These cells expressed pSTAT6 and YM1/FXIIIA on treatment with IL4 followed by DMSO, indicating M2 polarization via IL4/STAT6 signalling pathway. Kadoch, 2009. When they were treated with IL4 followed by 4-amino-2-(2,6-dioxo-piperidine-3-yl)-isoindoline-1,3-dione, they expressed pSTAT1 and iNOS, and did not express pSTAT6 and YM1/FXIIIA, indicating conversion of their polarization from M2 to M1 via activation of STAT1 signalling and inactivation of STAT6 signalling. As such, 4-amino-2-(2,6-dioxo-piperidine-3-yl)-isoindoline-1,3-dione was able to reverse IL4-induced M2 polarization of macrophages and convert them into M1-polarized state.

To elucidate the impact of 4-amino-2-(2,6-dioxo-piperidine-3-yl)-isoindoline-1,3-dione on lymphoma-associated macrophages, cell culture experiments were performed using three human cell lines: lymphoma cell lines (Raji or OCI-LY10) and human monocyte cell line (U937) were cultured with or without human NK cell line (YTS). When U937 cells were cocultured with lymphoma cells (see FIGS. 7A & 8A), they became M2 polarized with expression of pSTAT6 and FXIIIA. 4-amino-2-(2,6-dioxo-piperidine-3-yl)-isoindoline-1,3-dione treatment prevented the M2 polarization of macrophages but did not induce them into M1 polarization. In triple cell culture experiments with YTS cells, lymphoma cells, and U937 (see FIGS. 7B & 8B), U937 cells became M2-polarized; upon 4-amino-2-(2,6-dioxo-piperidine-3-yl)-isoindoline-1,3-dione treatment, they became M1-polarized with expression of pSTAT1 and iNOS. Based on these results, 4-amino-2-(2,6-dioxo-piperidine-3-yl)-isoindoline-1,3-dione treatment has a major impact on the polarization status of tumor-associated macrophages, inhibiting their M2 polarization and, in the presence of NK cells, converting their polarization from M2 to M1.

To further confirm the above findings and simulate what happened in pre-clinical in-vivo studies, cell culture experiments were performed in which primary murine microglial cells and lymphoma cells were co-cultured with or without primary murine NK cells. Essentially similar findings were observed. When primary microglial cells were co-cultured with lymphoma cells (Raji or OCI-LY10) (see FIGS. 13A & 14A), they became M2 polarized with expression of Ym1 and pSTAT6. When the co-culture was treated with 4-amino-2-(2,6-dioxo-piperidine-3-yl)-isoindoline-1,3-dione, M2 polarization was not seen in microglial cells: and there was also no evidence of M1 polarization. In triple cell culture experiments with primary NK cells, lymphoma cells, and primary microglial cells (see FIGS. 13B & 14B), microglial cells became M2-polarized. With 4-amino-2-(2,6-dioxo-piperidine-3-yl)-isoindoline-1,3-dione treatment, microglial cells became M1-polarized with expression of pSTAT1 and iNOS. As such, 4-amino-2-(2,6-dioxo-piperidine-3-yl)-isoindoline-1,3-dione treatment prevented M2 polarization of microglial cells when they are co-cultured with lymphoma cells and converted their polarization from M2 to M1 polarization in the presence of NK cells.

To assess the functional impact of 4-amino-2-(2,6-dioxo-piperidine-3-yl)-isoindoline-1,3-dione on macrophages, phagocytosis assay was performed. The experiment showed that treatment of primary microglial cells and human monocytes (U937) with 4-amino-2-(2,6-dioxo-piperidine-3-yl)-isoindoline-1,3-dione significantly increased their phagocytic activity (see FIG. 9).

What is claimed is:

1. A method of increasing macrophages or natural killer cells in tumor microenvironment in a human having a central nervous system cancer, which comprises administering to a human in need thereof a therapeutically effective amount of 4-amino-2-(2,6-dioxo-piperidine-3-yl)-isoindoline-1,3-dione.

2. The method of claim 1, wherein the cancer is relapsed, refractory or resistant to conventional therapy.

3. The method of claim 1, wherein the cancer is primary central nervous system lymphoma ("PCNSL"), primary vitreoretinal lymphoma ("PVRL"), intra-ocular lymphoma, central nervous system blastoid mantle cell lymphoma, a central nervous system tumor, a central nervous system solid tumor, neuroblastoma, a central nervous system cancerous condition, mantle cell lymphoma ("MCL"), lymphocytic lymphoma of intermediate differentiation, intermediate lymphocytic lymphoma ("ILL"), diffuse poorly differentiated lymphocytic lymphoma ("PDL"), centrocytic lymphoma, diffuse small-cleaved cell lymphoma ("DSCCL"), follicular lymphoma, or mantle zone lymphoma.

4. The method of claim 1, where the cancer is a neuroepithelial tumor, a tumor of meninges, a nerve sheath tumor, glioblastoma, or astrocytoma.

5. The method of claim 4, wherein the cancer is a neuroepithelial tumor, and wherein the neuroepithelial tumor is an ependymal tumor.

6. The method of claim 1, wherein the cancer is a tumor of meninges, a neuroepithelial tumor, a nerve sheath tumor, glioblastoma, astrocytoma, a central nervous system lymphoma, hemangioma, or neoplasm.

7. The method of claim 6, wherein the cancer is a tumor of meninges.

8. The method of claim 1, wherein the cancer is located at meninges, pituitary, pineal, nasal cavity, frontal lobe, temporal lobe, parietal lobe, occipital lobe, cerebrum, ventricle, cerebellum, brain stem, spinal cord, cauda equina, or cranial nerves.

9. The method of claim 1, wherein the cancer is meningioma, glioblastoma, a tumor of the pituitary, a nerve sheath tumor, a neuroepithelial tumor, craniopharyngioma, a central nervous system lymphoma, a germ cell tumor, astrocytomas, oligodendrogliomas, or an embryonal tumor.

10. The method of claim 1, wherein the cancer is glioma.

11. The method of claim 10, wherein the glioma is glioblastoma, astrocytoma, an oligoastrocytic tumor, oligodendroglioma, an ependymal tumor, or glioma malignant NOS.

12. The method of claim 1, where the cancer is a central nervous system lymphoma.

13. The method of claim 12, where the central nervous system lymphoma is primary central nervous system lymphoma ("PCNSL").

14. The method of claim 1, wherein the amount of 4-amino-2-(2,6-dioxo-piperidine-3-yl)-isoindoline-1,3-dione administered is from about 0.1 to about 5 mg per day.

15. The method of claim 14, wherein the amount of 4-amino-2-(2,6-dioxo-piperidine-3-yl)-isoindoline-1,3-dione administered is about 1, 2, 3 or 4 mg per day.

16. The method of claim 15, wherein the amount of 4-amino-2-(2,6-dioxo-piperidine-3-yl)-isoindoline-1,3-dione administered is about 4 mg per day.

17. The method of claim 14, wherein 4-amino-2-(2,6-dioxo-piperidine-3-yl)-isoindoline-1,3-dione administered is enantiomerically pure.

18. The method of claim 17, wherein 4-amino-2-(2,6-dioxo-piperidine-3-yl)-isoindoline-1,3-dione administered is S enantiomer.

19. The method of claim 17, wherein 4-amino-2-(2,6-dioxo-piperidine-3-yl)-isoindoline-1,3-dione administered is R enantiomer.

20. The method of claim 14, wherein 4-amino-2-(2,6-dioxo-piperidine-3-yl)-isoindoline-1,3-dione is administered orally.

21. The method of claim 20, wherein 4-amino-2-(2,6-dioxo-piperidine-3-yl)-isoindoline-1,3-dione is administered in the form of a capsule or tablet.

22. The method of claim 14, wherein 4-amino-2-(2,6-dioxo-piperidine-3-yl)-isoindoline-1,3-dione is administered for 21 days followed by seven days rest in a 28 day cycle.

23. The method of claim 22, wherein 4-amino-2-(2,6-dioxo-piperidine-3-yl)-isoindoline-1,3-dione is administered in an amount of from about 1 mg to about 4 mg per day for 21 days followed by seven days rest in a 28 day cycle.

24. The method of claim 23, further comprising administration of rituximab in an amount of 375 mg/m$^2$ by intravenous infusion weekly.

25. A method of increasing macrophages or natural killer cells in tumor microenvironment in a human having a central nervous system cancer, which comprises administering to a patient in need thereof a therapeutically effective amount of 4-amino-2-(2,6-dioxo-piperidine-3-yl)-isoindoline-1,3-dione and a therapeutically effective amount of a second active agent.

26. The method of claim 25, wherein the second active agent is antibody, hematopoietic growth factor, cytokine, anti-cancer agent, antibiotic, cox-2 inhibitor, immunomodulatory agent, immunosuppressive agent, corticosteroid, or a pharmacologically active mutant or derivative thereof.

27. The method of claim 25, wherein the second active agent is rituximab.

* * * * *